(12) United States Patent
Snyders

(10) Patent No.: US 6,821,297 B2
(45) Date of Patent: Nov. 23, 2004

(54) ARTIFICIAL HEART VALVE, IMPLANTATION INSTRUMENT AND METHOD THEREFOR

(76) Inventor: Robert V. Snyders, 1638 Wolf Trail Rd., Ballwin, MO (US) 63021

(*) Notice: Subject to any disclaimer, the term of this patent is extended or adjusted under 35 U.S.C. 154(b) by 72 days.

(21) Appl. No.: 10/135,746

(22) Filed: Apr. 30, 2002

(65) Prior Publication Data

US 2002/0123802 A1 Sep. 5, 2002

Related U.S. Application Data

(63) Continuation-in-part of application No. 09/775,360, filed on Feb. 1, 2001, now Pat. No. 6,540,782.
(60) Provisional application No. 60/179,853, filed on Feb. 2, 2000.

(51) Int. Cl.[7] .................................................. A61F 2/06
(52) U.S. Cl. ...................................................... 623/2.18
(58) Field of Search ................................ 623/2.1, 2.11, 623/2.13, 2.14, 2.15, 2.16, 2.18, 2.19, 2.12

(56) References Cited

U.S. PATENT DOCUMENTS

| | | |
|---|---|---|
| 4,339,831 A | 7/1982 | Johnson |
| 5,332,402 A | 7/1994 | Teitelbaum |
| 5,397,351 A | 3/1995 | Pavcnik et al. |
| 5,411,552 A | 5/1995 | Andersen et al. |
| 5,413,599 A | 5/1995 | Imachi et al. |
| 5,545,214 A | 8/1996 | Stevens |
| 5,855,601 A | 1/1999 | Bessler et al. |
| 5,861,028 A | 1/1999 | Angell |

FOREIGN PATENT DOCUMENTS

| | | |
|---|---|---|
| DE | 41 01 935 A 1 | 7/1992 |
| WO | WO99/13801 | 3/1999 |

OTHER PUBLICATIONS

H.R. Andersen, et al., *Transluminal Implantation of Artificial Heart Valves. Description of a New Expandable Aortic Valve and Initial Results with Implantation by Catheter Technique in Closed Chest Pigs*, 13 European Heart Journal 704–708 (1992).

Steven R. Bailey, *Percutaneous Expandable Prosthetic Valves*, Textbook of Interventional Cardiology 1268–76 (1995).

Dwight E. Harken, et al., *Partial and Complete Prostheses in Aortic Insufficiency*, 40 J. Thoracic and Cardiovas. Surg. 744–62 (1960).

(List continued on next page.)

*Primary Examiner*—Corrine McDermott
*Assistant Examiner*—William Matthews
(74) *Attorney, Agent, or Firm*—Sonnenschein Nath & Rosenthal LLP

(57) ABSTRACT

An artificial valve for repairing a damaged heart valve having a plurality of cusps separating upstream and downstream regions. The artificial valve includes a flexibly resilient frame with a plurality of peripheral anchors for anchoring the frame in position between the regions. The frame includes a central portion located between the anchors. The valve includes a flexible valve element attached to the central portion of the frame having an upstream side and a downstream side opposite the upstream side. The valve element moves to an open position when fluid pressure in the upstream region is greater than fluid pressure in the downstream region to permit downstream flow. The valve element moves to a closed position when fluid pressure in the downstream region is greater than fluid pressure in the upstream region to prevent flow reversal. The valve may be used in beating heart procedures, avoiding cardiopulmonary bypass and cardioplegia.

46 Claims, 11 Drawing Sheets

OTHER PUBLICATIONS

Stephen L. Hilbert, et al., *Evaluation of Explanted Polyurethane Trileaflet Cardiac Valve Prostheses*, 94 J. Thorac Cardiovac Surg 419–29 (1987).

Charles A. Hufnagel, *Basic Concepts in the Development of Cardiovascular Prostheses*, 137 Great Ideas in Surgery 285–300 (Mar. 1979).

L.L. Knudsen, et al., *Catheter–implanted Prosthetic Heart Valves* 18 The International Journal of Artificial Organs 253–262 (1993).

H.B. Lo, et al. *A Tricuspid Polyurethane Heart Valve as an Alternative to Mechanical Prostheses or Bioprostheses*, XXXIV Trans. Am. Soc. Artif. Intern. Organs 839–44 (1988).

St. Jude Medical Heart Valve Division, *The Right Choice for all the Right Reasons*, (1999).

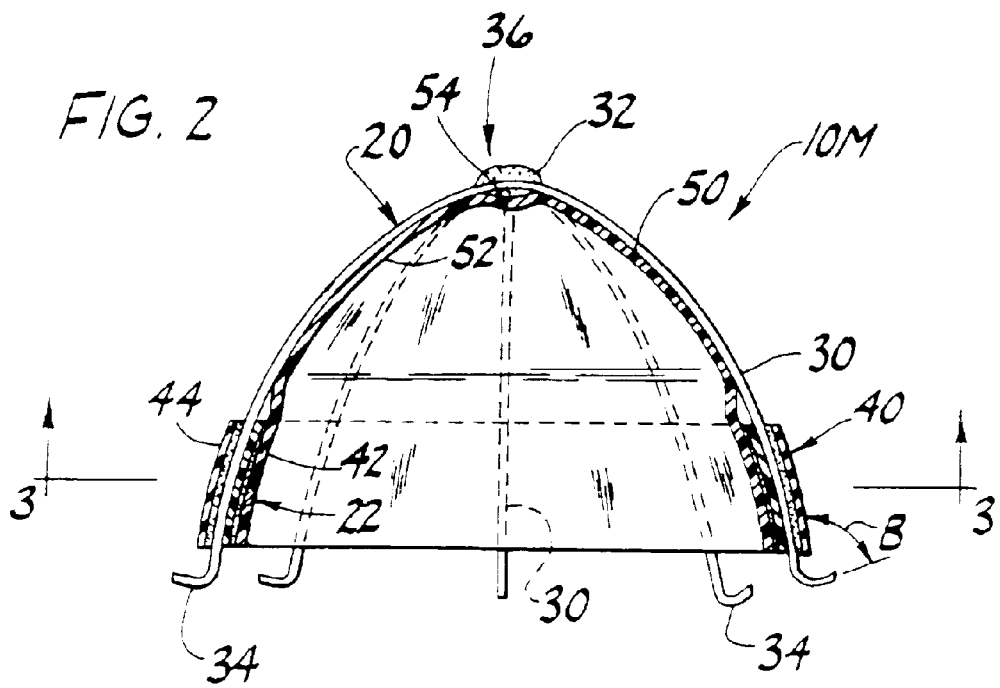
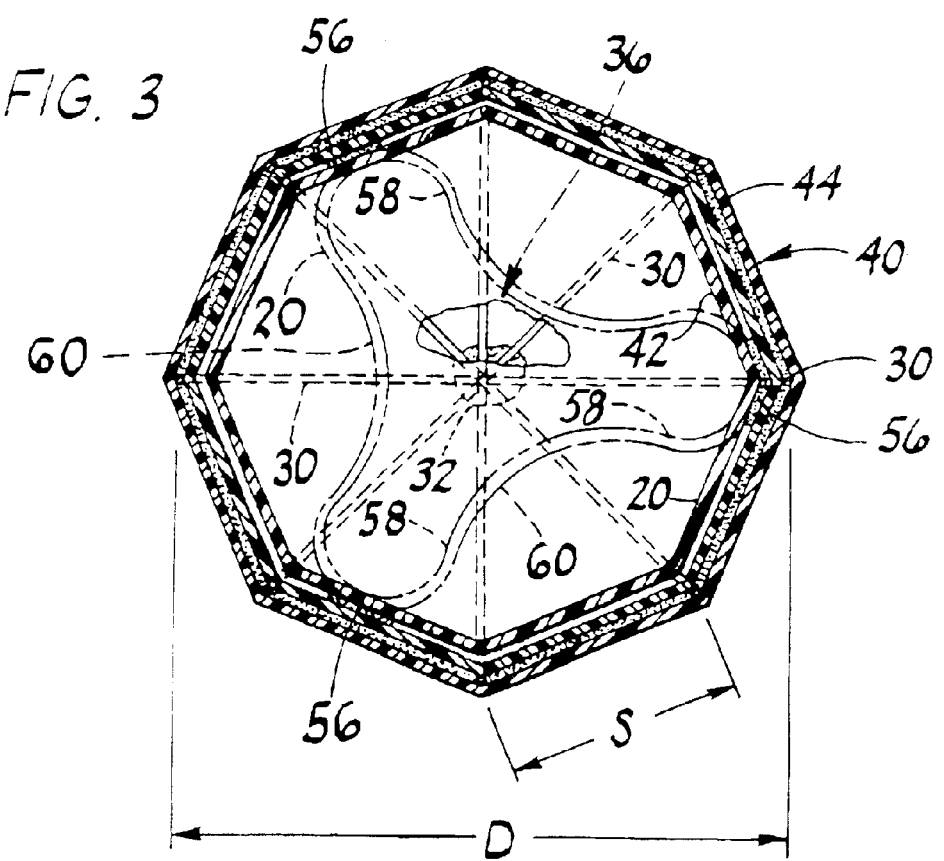

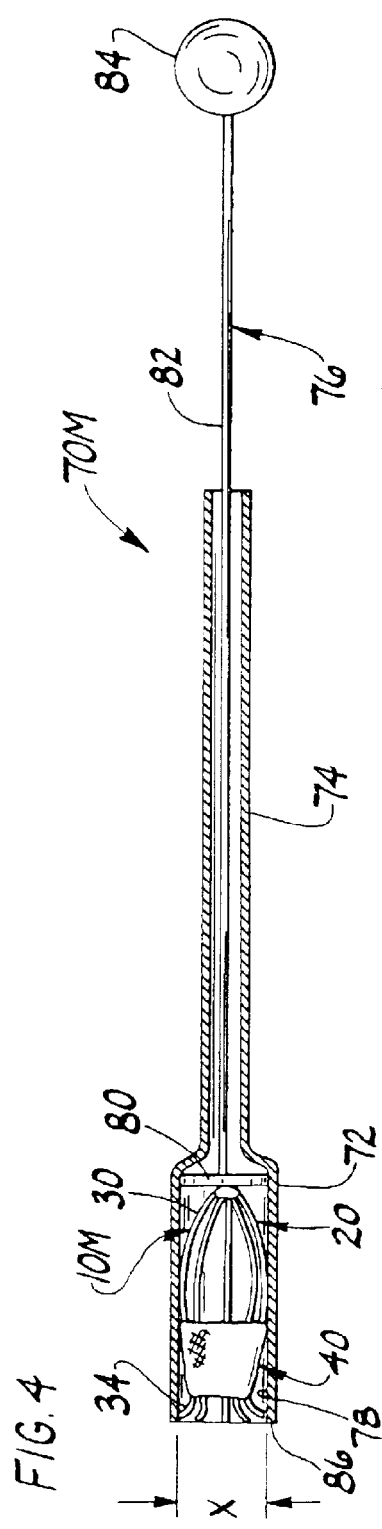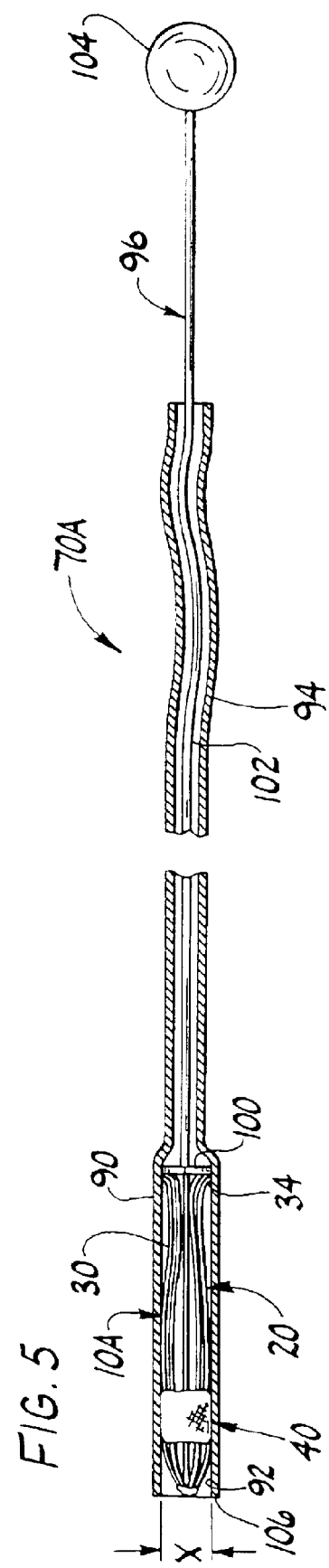

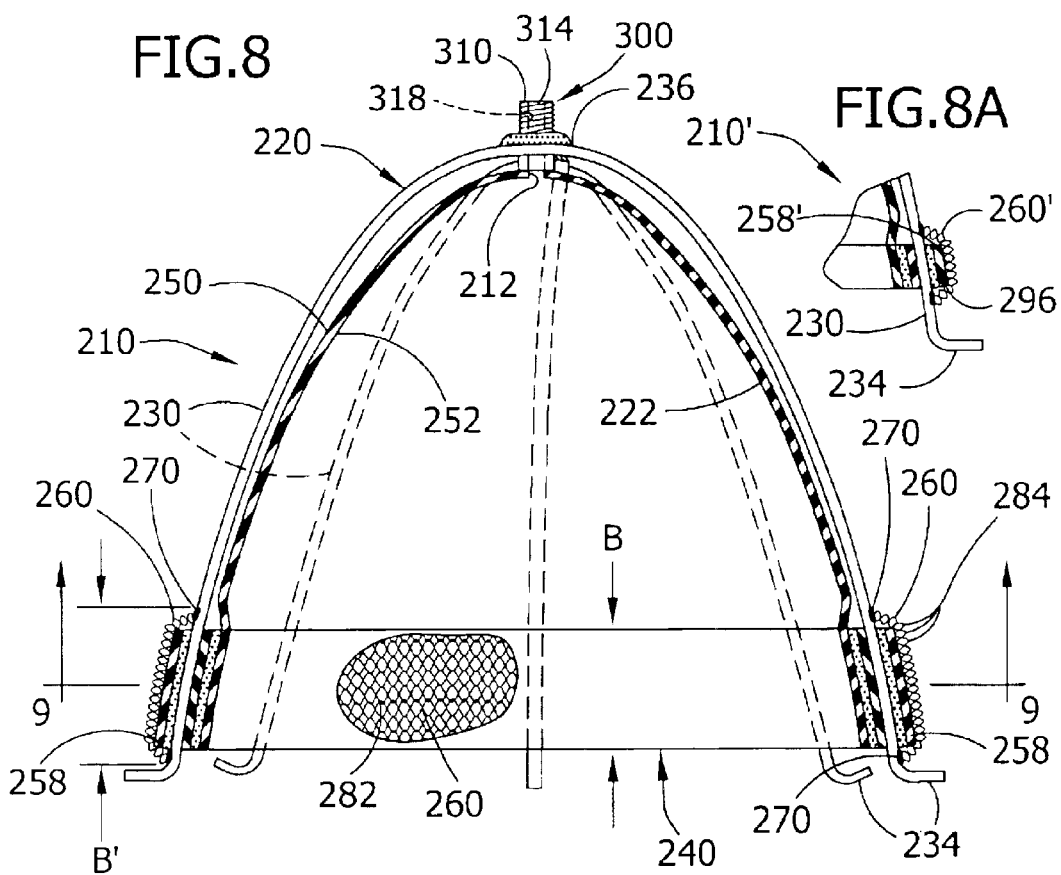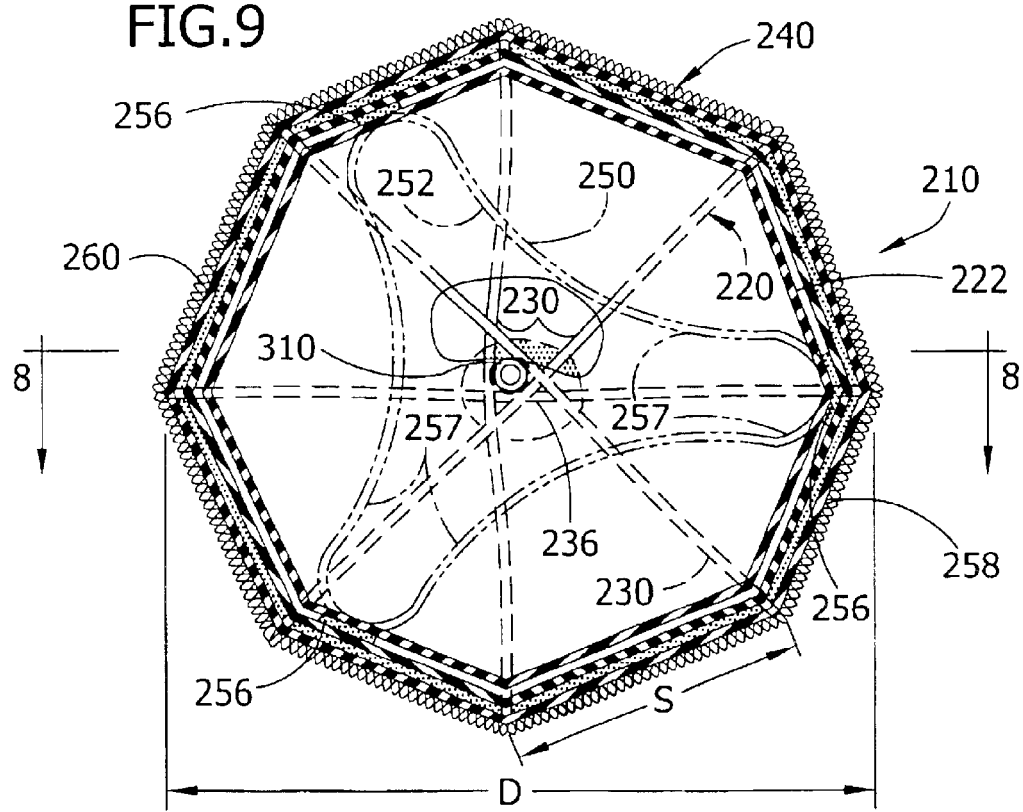

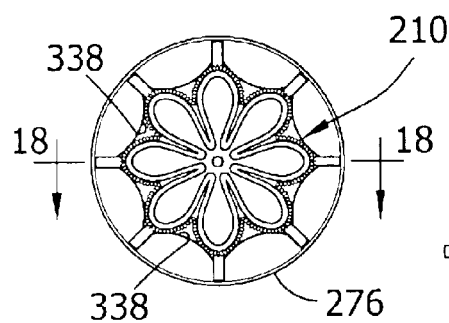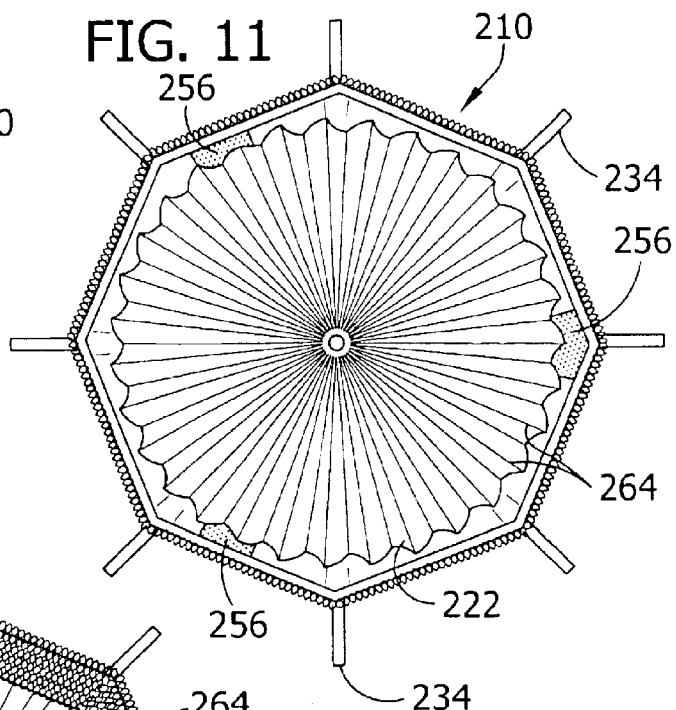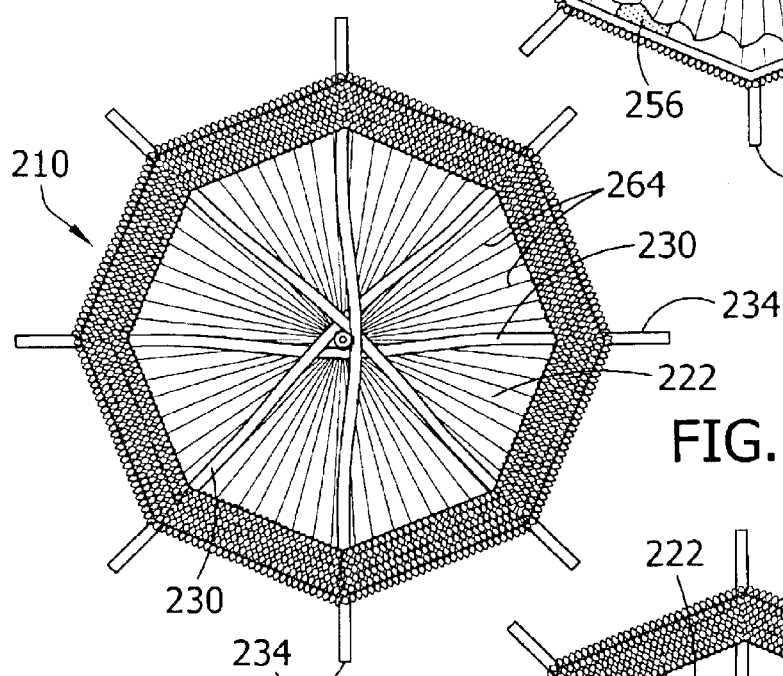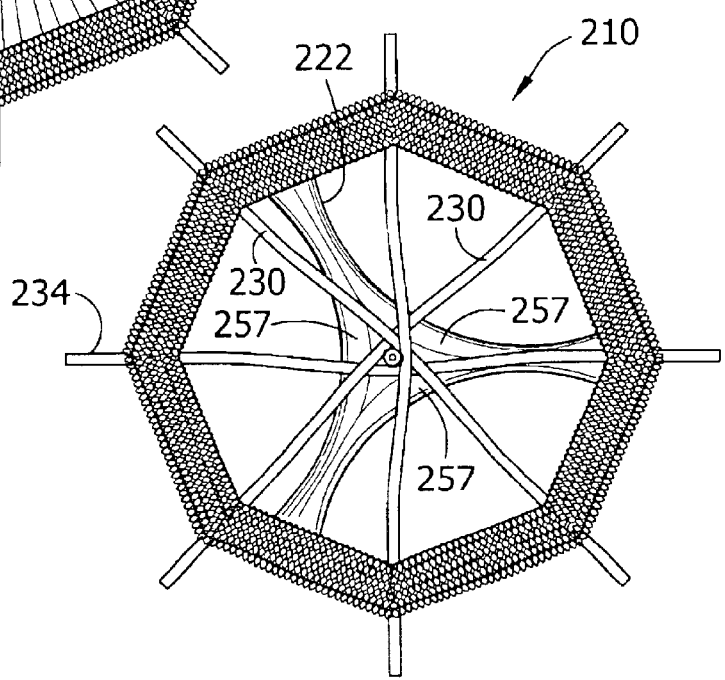

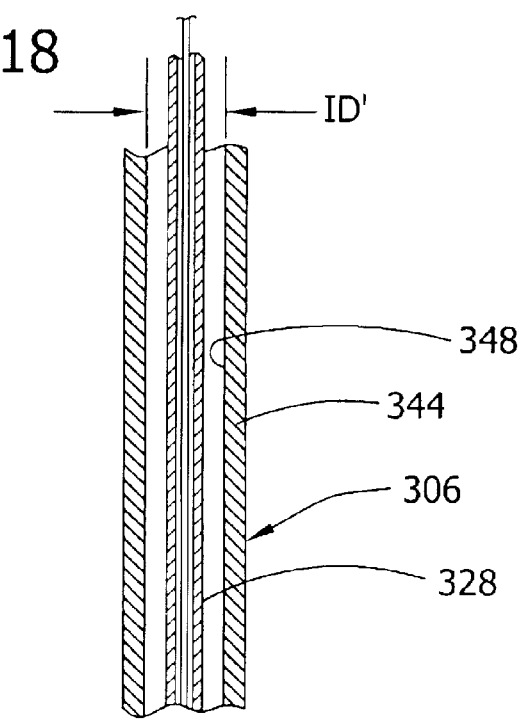
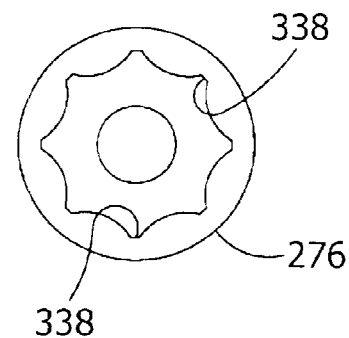
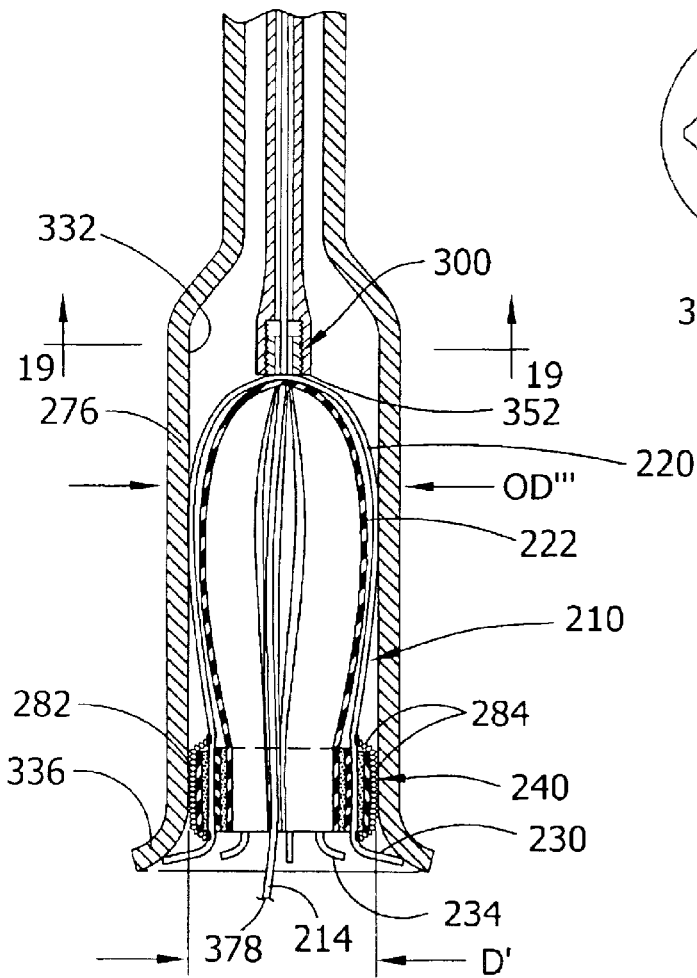
FIG. 18
FIG. 19

ARTIFICIAL HEART VALVE, IMPLANTATION INSTRUMENT AND METHOD THEREFOR

CROSS-REFERENCE TO RELATED APPLICATION

This application is a continuation-in-part of Utility Patent application Ser. No. 09/775,360 filed Feb. 1, 2001, now U.S. Pat. No. 6,540,782, which claims benefit of Provisional Patent Application No. 60/179,853 filed Feb. 2, 2000, both of which are hereby incorporated by reference.

BACKGROUND OF THE INVENTION

The present invention relates generally to valve implants, and more particularly to artificial heart valves for repairing damaged heart valves.

A human heart has four chambers which alternately expand and contract to pump blood through the vessels of the body. The heart also includes a check valve at the upstream end of each chamber to ensure that blood flows in the correct direction through the body as the heart chambers expand and contract. These valves sometimes become damaged resulting in their inability to close when the downstream chamber contracts. When the valves do not close, blood flows backward through the valve resulting in diminished blood flow and lower blood pressure. The valves can also become damaged so they do not open sufficiently thereby resulting in diminished downstream blood flow.

Although replacement valves and surgical procedures have been developed to alleviate these conditions, they have significant drawbacks. Many earlier valves require invasive implantation techniques in which the chest is opened, the ribs are spread, the heart is paralyzed, and following cardio-pulmonary bypass, the heart is cut open to implant the valve. These invasive techniques are stressful on the patient, increase the opportunity for infection and slow recovery. As a result, valves which may be implanted with non-invasive techniques have been developed. These valves are implanted by transluminal or endothoracoscopic techniques which reduce many of the drawbacks associated with invasive surgery. However, many of these valves also require the damaged native heart valve be removed prior to implanting the artificial valve. Removing the native valve increases the risk that a portion of the valve will migrate through the body and block vessels downstream from the heart.

Many mechanical and bioprosthetic valves have been developed to replace native heart valves. See C. A. Hufnagel, *Basic Concepts in the Development of Cardiovascular Prostheses,* 137 Am. J. of Surg. at 285–300 (1972). See also D. E. Harken et al., *Partial and Complete Prosthesis in Aortic Insufficiency,* 40 J. Thorac & Cdvsc Surg., no. 6., at 744–62 (1960). These valves include ball-valve prostheses, flap-valve prostheses, polymeric trileaflet synthetic valves, and bioprosthetic valves made from animal allograft tissues such as pig valves and preserved heterologous bovine and porcine pericardial tissue valves. See H. B. Lo et al., *A Tricuspid Polyurethane Heart Valve as an Alternative to Mechanical Prostheses or Bioprostheses,* 34 Trans. Am. Soc. of Art. Int. Organs at 839–44 (1988); and S. L. Hilbert et al., *Evaluation of Explanted Polyurethane Trileaflet Cardiac Valve Prostheses,* 94 J. Thorac & Cdvsc Surg. at 419–29 (1987). Most of the aforementioned valves require open chest surgery and cardiopulmonary bypass for implantation.

More recently percutaneous and transluminal implantation have been suggested. See Steven R. Bailey, *Percutaneous Expandable Prosthetic Valves* Textbook of Interventional Cardiology, chap. 75 (1995)(referencing work of Andersen et al.) See also Knudsen et al., *Catheter-implanted Prosthetic Heart Valves,* 6 Int'l J. of Art. Organs, no. 5, at 253–62 (1993); Knudsen et al. *Transluminal Implantation of Artificial Heart Valves. Description of New Expandable Aortic Valve and Initial Results With Implantation by Catheter Technique in Closed Chest Pigs,* 13 European Heart J. at 704–08 (1992); and U.S. Pat. No. 5,411,552 (Andersen). The Andersen device includes a heterologous pig valve mounted in an annular ring. Due to the size of this device, it must be implanted by direct abdominal aortic incision and entry. Further, the Andersen device requires a separate inflating balloon for its deployment. U.S. Pat. No. 5,397,351 (Pavcnik) describes an expandable caged poppet for percutaneous implantation in an aortic valve site. However, the size of the Pavcnik device makes percutaneous implantation difficult. U.S. Pat. No. 5,885,601 (Bessler) describes a transluminal valve implantation but does not describe the specific valve construction. The Bessler procedure includes excision, vacuum removal of the native valve, cardiopulmonary bypass and backflushing of the coronary arterial tree.

SUMMARY OF THE INVENTION

Among the several objects and features of the present invention may be noted the provision of an artificial heart valve which accommodates implantation without removing the damaged native heart valve; the provision of a valve which may be implanted using non-invasive surgery; the provision of a valve which permits implantation without the need for cardio-pulmonary bypass; the provision of a valve which permits implantation by conventional open chest surgery and cardio-pulmonary bypass; provision of a valve which allows for repositioning the valve during implantation; and the provision of a valve which allows for guiding the valve to the point of implantation along a guide.

Generally, an artificial valve of the present invention repairs a damaged heart valve having a plurality of cusps separating an upstream region from a downstream region. The artificial valve comprises a flexibly resilient frame sized and shaped for insertion in a position between the upstream region and the downstream region. The frame has a plurality of peripheral anchors for anchoring the frame in the position between the upstream region and the downstream region and a central portion located between the plurality of peripheral anchors. A flexible valve element attaches to the central portion of the frame having an upstream side facing the upstream region when the frame is anchored in the position between the upstream region and the downstream region and a downstream side opposite the upstream side facing the downstream region when the frame is anchored in the position between the upstream region and the downstream region. The valve element moves in response to a difference between fluid pressure in the upstream region and fluid pressure in the downstream region between an open position, in which the element permits downstream flow between the upstream region and the downstream region, and a closed position, in which the element blocks flow reversal from the downstream region to the upstream region. The valve element moves to the open position when fluid pressure in the upstream region is greater than fluid pressure in the downstream region, permitting downstream flow from the upstream region to the downstream region. The valve element moves to the closed position when fluid pressure in the downstream region is greater than fluid pressure in the upstream region, preventing flow reversal from the downstream region to the upstream region. An opening extends through at least one of the frame and the valve element for receiving an implement.

In a second embodiment of the present invention, an artificial valve includes a flexibly resilient frame having a plurality of peripheral anchors for anchoring the frame in the position between the upstream and the downstream region. A flexible valve element attaches to the frame having a convex upstream side and a concave downstream side. An opening extends through at least one of the frame and the valve element.

The present invention is also directed to a combination of an artificial valve, including a frame, a valve element, an opening and a flexible, elongate guide sized for receipt within the opening to guide the valve into position.

Another aspect of the present invention is directed to a combination of an artificial valve, including a frame and valve element, and an instrument including a holder, an elongate manipulator and an installer. The holder has a hollow interior sized for holding the artificial valve when the frame is in a collapsed configuration. The elongate manipulator attaches to the holder for manipulating the holder into position between the upstream region and the downstream region. The installer is received within the hollow interior of the holder and is releasably attachable to the frame of the artificial heart valve for maneuvering the artificial heart valve from the hollow interior of the holder into position between the upstream region and the downstream region.

The present invention is also directed to an endothoracoscopic method of inserting an artificial valve between a plurality of cusps of a damaged heart valve. The method comprises the steps of making an opening in a chest wall of a patient and making an incision in a heart of the patient. An end of an elongate instrument is inserted through the opening made in the chest wall and the incision made in the heart. The inserted end of the instrument is positioned adjacent the plurality of cusps of the damaged heart valve. An artificial valve is ejected from the end of the instrument positioned adjacent the plurality of cusps of the damaged heart valve into a position between the plurality of cusps of the damaged heart valve without removing the damaged heart valve from the heart. The artificial valve is then retrieved into the end of the instrument and the inserted end of the instrument is repositioned adjacent the plurality of cusps of the damaged heart valve. The repositioned artificial valve is ejected from the end of the instrument positioned adjacent the plurality of cusps of the damaged heart valve into position between the plurality of cusps of the damaged heart valve without removing the damaged heart valve from the heart.

Another aspect of the present invention is directed to a transluminal method of inserting an artificial valve between a plurality of cusps of a damaged heart valve, including the steps of ejecting, retrieving, repositioning and a second ejecting step. The method further comprises making an incision in a vessel leading to the heart and inserting an end of an elongate flexible instrument through the incision made in the vessel. The method further comprises pushing the end of the instrument through the vessel and positioning the end adjacent the plurality of cusps of the damaged heart valve.

The present invention is also directed to a transluminal method of inserting an artificial valve between a plurality of cusps of a damaged heart valve, including the steps of making, inserting and ejecting. The method further comprises inserting an end of a guide through the incision made in the vessel, pushing the guide through the vessel, threading an elongate flexible instrument having a hollow interior onto the guide and pushing the end of the instrument through the vessel along the guide until the end is adjacent the plurality of cusps of the damaged heart valve.

Other objects and features of the present invention will be in part apparent and in part pointed out hereinafter.

BRIEF DESCRIPTION OF THE DRAWINGS

FIG. 2 is a vertical cross section of an artificial valve;

FIG. 3 is a cross section of the valve taken in the plane of line 3-3 of FIG. 2;

FIG. 4 is a vertical cross section of an instrument for implanting a valve using an endothoracoscopic procedure of the present invention;

FIG. 5 is a vertical cross section of an instrument for implanting a valve using a transluminal procedure of the present invention;

FIG. 8 is a front elevation of the artificial valve of FIG. 7 in partial section;

FIG. 8A is an enlarged partial section of an alternative embodiment of the artificial valve illustrated in FIG. 8;

FIG. 9 is a cross section of the valve of FIG. 8 taken in the plane of line 9—9 of FIG. 8;

FIG. 10 is an enlarged end view of an instrument with an artificial valve;

FIG. 11 is a bottom plan of an artificial valve having a pleated valve member in its expanded configuration;

FIG. 12 is a top plan of the valve of FIG. 11;

FIG. 13 is a top plan of the valve of FIG. 12 with the valve member collapsed inward to allow flow through the valve;

FIG. 18 is an enlarged section of an instrument with the artificial valve and installer taken in the plane of line 18-18 of FIG. 10; and FIG. 19 is a cross section of the instrument of FIG. 18 with the artificial valve and installer removed.

Corresponding reference characters indicate corresponding parts throughout the several views of the drawings.

DETAILED DESCRIPTION OF THE PREFERRED EMBODIMENT

Figure 1:
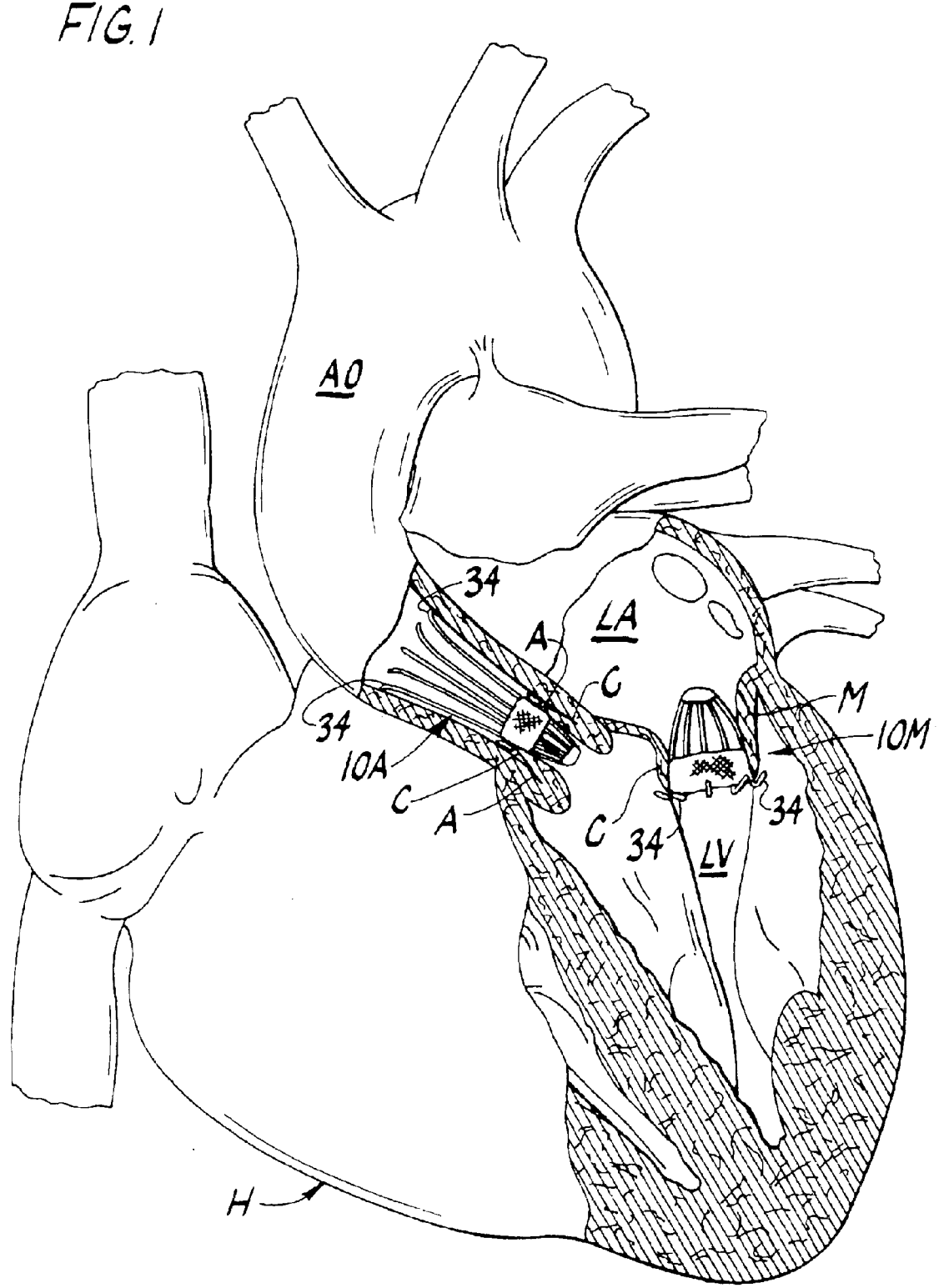
FIG. 1 is a front elevation of a heart in partial section showing two artificial valves of the present invention.

Referring now to the drawings and in particular to FIG. 1, artificial heart valves of the present invention are designated in their entireties by the reference numbers 10A and 10M. The artificial valve 10A is specifically configured for repairing a damaged aortic valve A of a heart, generally designated by H. The artificial valve 10M is specifically configured for repairing a damaged mitral valve M. In addition, an artificial valve having a configuration similar to valve 10A may be used to repair a damaged pulmonary heart valve (not shown), and a valve having a configuration similar to valve 10M may be used to repair a damaged tricuspid heart valve (not shown). Each native heart valve (e.g., mitral valve M) normally has two cusps C (or three cusps in the case of the tricuspid valve) separating an upstream region (e.g., the left atrium LA) of the heart H from a downstream region (e.g., the left ventricle LV) of the heart positioned downstream from the upstream region. In use, the artificial heart valves (e.g., the artificial heart valve 10M) are positioned between the upstream region and the downstream region, preferably between the cusps C of the respective native valve (e.g., the mitral valve M), to ensure blood flows through the heart H in the appropriate direction as will be explained in greater detail below.

As illustrated in FIG. 2, the artificial valve 10M comprises a flexibly resilient external frame, generally designated by 20, and a flexible valve element, generally designated by 22. The frame 20 includes a plurality of U-shaped stenting elements 30. Each of the U-shaped elements 30 has a length extending between opposite ends. Although the elements 30 may have other lengths without departing from the scope of the present invention, the elements of the preferred embodiment have approximately equal lengths. Further, the elements 30 are joined generally midway between their respective ends at a junction 32 of the elements. Although four frame elements 30 are shown in FIGS. 2 and 3, the valve 10M may have fewer or more elements without departing from the scope of the present invention. Preferably, the stenting elements 30 are sufficiently compressible to permit the valve 10M to be compressed to a configuration such as shown in FIG. 4 during implantation in the respective heart valve as will be explained below. Still further, the stenting elements 30 preferably are sufficiently resilient to hold the artificial valve 10M in position between the cusps C of the native valve M after implantation and to hold the cusps of the native valve open. As used herein, the term "stenting" is intended to convey that the element 30 holds the cusps C of the native valve at least partially open.

Although the elements 30 of the preferred embodiment are made of nickel alloy wire, such as Nitinol superelastic alloy wire, available from Unitek Corp. of Monrovia, Calif., other materials may be used without departing from the scope of the present invention. The Nitinol may additionally include a PTFE (polytetrafluoroethylene) coating. Further, although the wire of the preferred embodiment has a rectangular cross section with dimensions of about 0.50 mm by about 0.762 mm, wires having other shapes and sizes may be used without departing from the scope of the present invention. In addition, the frame 20 may be of unitary construction. For instance, a small diameter tube of Nitinol or other appropriate material may have longitudinal slits extending from one end of the tube nearly to the opposite end, thereby forming multiple portions cantilevered from one end. Such cantilevered portions may be bent outward to form the frame of the artificial valve.

A peripheral anchor 34 is formed at each end of the frame elements 30. As illustrated in FIG. 1, these anchors 34 are used to attach the frame 20 between the plurality of cusps C of the damaged valve (e.g., the mitral valve M) in a position between an upstream region and a downstream region. Although other conventional anchor formations may be used without departing from the scope of the present invention, the anchors 34 of the preferred embodiment are hooks. It is envisioned the anchors 34 may also include conventional barbs (not shown) for preventing the hooks from being dislodged from the heart H after implantation. Further, as illustrated in FIG. 2, in the most preferred embodiment the hooks form an angle B of between about 55 degrees and about 80 degrees with the ends of the frame elements 30. In addition, the frame 20 includes a central portion, generally designated by 36, located between the plurality of peripheral anchors 34.

As further shown in FIG. 2, a band, generally designated by 40, extends around the frame 20 between each of the frame elements 30. The band 40 extends between each frame element 30 and an adjacent frame element to limit maximum spacing S between the frame elements and to shape and cooperate with the elements to create a structurally sound frame construction. The band 40 permits the frame elements 30 to be pushed together so the flexibly resilient frame 20 can be collapsed to a collapsed configuration as shown in FIGS. 4 and 5. Depending upon the procedure which is intended to be used when implanting the valve, the frame 20 collapses to configurations having different maximum widths X. For instance, if the artificial valve (e.g., 10M) is implanted using endothoracoscopic methods, the maximum width X is less than about 18 mm and more preferably between about 12 mm and about 18 mm. However, if the valve (e.g., the artificial valve 10A) is implanted through a smaller blood vessel, such as transvenously or transluminally, the maximum width X must be smaller. For instance, the maximum width X must be between about 4 mm and about 8 mm, more preferably between about 6 mm and about 8 mm and still more preferably about 6 mm. Thus, the frame 20 is sized and shaped for insertion between the plurality of cusps C of the damaged heart valve in a position between an upstream region and a downstream region. Further, because the frame 20 is flexible, it expands to an expanded configuration as shown In FIG. 2 when not collapsed. When in the expanded configuration, the frame 20 has different sizes depending upon which native valve it is intended to replace. For instance, if the artificial valve is intended to repair a damaged mitral valve M or a tricuspid valve, the opposite ends of the frame elements 30 are spaced by a distance D of between about 2 cm and about 5 cm. If the artificial valve is intended to repair a damaged aortic valve A or a pulmonary valve, preferably the opposite ends of the frame elements 30 are spaced by a distance D of between about 2 cm and about 3 cm.

Although the band 40 may be made of other materials, such as heterologous animal pericardium (e.g., bovine or porcine pericardium) or autologous tissue engineered substrates, without departing from the scope of the present invention, the band of the preferred embodiment is made of a biocompatible, radiopaque, elastic material such as silicone rubber or polyurethane or polytetrafluoroethylene. Further, although the band 40 may have other constructions without departing from the scope of the present invention, the band of the preferred embodiment comprises an internal strip 42 and an external strip 44 joined in face-to-face relation. Although the band 40 may be attached to the frame elements 30 by other means, in the most preferred embodiment, the internal and external strips 42, 44, respectively, are adhesively bonded to the frame elements and to each other. Further, although the band 40 illustrated in FIG. 2 is substantially cylindrical, it is envisioned the band may have other shapes without departing from the scope of the present invention. For example, it is envisioned the band 40 may include a rim or flange (not shown) surrounding the valve adjacent the hooks for engaging the cusps C. It is also envisioned that an exterior surface of the band 40 may include a continuous or interrupted sheath of Dacron® velour material, porous PTFE (polytetrafluoroethylene) felt or the like to provide sites for vascular connective tissue ingrowth to enhance stability of the device after its implantation. (Dacron is a U.S. federally registered trademark of E.I. duPont de Nemours and Company of Wilmington, Del.)

The flexible valve element 22 is disposed within the frame 20 and attached to the central portion 36 of the frame. The valve element 22 has a convex upstream side 50 facing an upstream region (e.g., the left atrium LA) when the frame 20 is anchored between the cusps C of the damaged heart valve (e.g., mitral valve M) in a position between the upstream region and a downstream region; and a concave downstream side 52 opposite the upstream side facing the downstream region (e.g., the left ventricle LV) when the frame 20 is anchored between the cusps of the damaged heart valve in a position between the upstream region and the downstream region. The valve element 22 moves in response to differences between fluid pressure in the upstream region and the downstream region between an open position (as shown in phantom lines in FIG. 3) and a closed position (as shown in solid lines in FIG. 3). When the valve element 22 is in the open position, with the valve element 22 collapsed inward, it permits flow between the upstream region and the downstream region. When in the closed position, with the valve element 22 extended outward, the element 22 blocks flow between the upstream and downstream regions. The valve element 22 moves to the open position, with the element collapsed inward, when fluid pressure in the upstream region is greater than fluid pressure in the downstream region to permit downstream flow from the upstream region to the downstream region. The valve element 22 moves to the closed position, with the element extended outward, when fluid pressure in the downstream region is greater than fluid pressure in the upstream region to prevent flow reversal from the downstream region to the upstream region. Although the valve element 22 may be made of other materials without departing from the scope of the present invention, the valve element of the preferred embodiment is made of a biocompatible elastic material such as silicone rubber, polyurethane, PTFE, heterologous animal pericardium (e.g., bovine or porcine pericardium), or autologous tissue engineered substrates. Further, although the valve element 22 may have other thicknesses without departing from the scope of the present invention, the valve element of the preferred embodiment has a thickness of between about 0.127 mm and about 0.381 mm. In addition, it is envisioned the valve element 22 may be longitudinally pleated, as discussed in more detail below, without departing from the scope of the present invention (FIGS. 11–13). Without wishing to be bound by any particular theory, it is envisioned that longitudinal pleats may encourage laminar flow through the valve when in the open position, with the valve element collapsed inward.

The upstream side 50 of the flexible valve element 22 has an apex 54 which is attached to the frame 20 at the junction 32 of the elements 30. As illustrated in FIG. 3, the flexible valve element 22 is attached to the central portion 36 of the frame 20 at a position substantially centered between the anchors 34. Although the valve element 22 may be attached to the frame 20 by other means without departing from the scope of the present invention, the valve element of the preferred embodiment is attached to the frame by adhesive bonding. Further, the flexible valve element 22 is attached to the frame 20, and more particularly to the band 40, at several attachment points 56 around the frame. Thus, the valve element 22 forms flaps 58 extending between adjacent attachment points 56. Each of the flaps 58 and a corresponding portion of the band 40 extending between adjacent attachment points 56 defines an opening 60 through the valve when the valve element 22 moves to the open position, with the flaps of the valve element collapsed inward. The artificial valve depicted in FIG. 3 depicts the preferred flap configuration, having three attachments points 56 and three flaps 58 spaced around the frame 20. It is contemplated that other numbers of attachment points 56 (e.g., 2, 4, 5, 6, etc.) may be used without departing from the scope of the present invention. Although the valve element 22 may be attached to the band 40 using other means, the valve element of the preferred embodiment is attached to the band by adhesive bonding.

As illustrated in FIGS. 4 and 5, the artificial valves 10M, 10A, respectively, are used in combination with instruments, generally designated by 70M, 70A, for inserting the artificial valve between the cusps C of damaged heart valves M, A. The instrument 70M shown in FIG. 4 is intended for use when implanting the valve 10M using an endothoracoscopic or transluminal procedure. It is envisioned this instrument would be used primarily when implanting an artificial valve in the mitral valve M, however similar instruments could be used to implant artificial valves in other native valves of the heart H such as the tricuspid or pulmonary valves. When used to implant an artificial valve in a mitral, tricuspid or pulmonary valve, the instrument could be introduced through a jugular or femoral vein. The endothoracoscopic instrument 70M comprises a tubular holder 72, and an elongate tubular manipulator 74 attached to the holder for manipulating the holder into position. Further, the instrument 70M includes an ejector, generally designated by 76, positioned in a hollow interior 78 of the holder 72 for ejecting the artificial heart valve 10M from the holder. The hollow interior 78 of the holder 72 is sized for holding the artificial valve 10M when the frame 20 is in the collapsed configuration (e.g., less than about 18 mm). Further, the hollow interior 78 may have axial grooves for receiving the anchors 34 of the valve to prevent the anchors from being tangled during valve implantation. Such grooves are described in greater detail below with respect to another embodiment. The manipulator 74 is a flexible tube attached to the holder 72 for manipulating the holder through an incision made in the heart H or selected vessel and into position adjacent the plurality of cusps C of the damaged heart valve. The ejector 76 includes a flat plunger tip 80 which engages the valve 10M, a push rod 82 attached to the tip for moving the tip forward in the holder 72 for ejecting the valve from the holder, and a handle 84 attached to the push rod opposite the plunger tip for gripping the ejector when ejecting the valve from the holder.

To implant an artificial valve 10M using the instrument 70M via an endothoracoscopic procedure, a small opening is made in a chest wall (or another vascular access site) of a patient and a small incision is made in a heart H of the patient. The holder end 86 of the instrument 70M is inserted through the opening made in the chest wall and the incision made in the heart H. The inserted end 86 of the instrument 70M is positioned adjacent the cusps C of the damaged heart valve M and the artificial valve 10M is ejected from the end of the instrument into a position between the cusps of the damaged valve as shown in FIG. 1. When ejecting the valve 10M from the end 86 of the instrument 70M, it is envisioned that the handle 84 of the ejector 76 will be held in place while the manipulator 74 and holder 72 are withdrawn to push the valve out of the holder. Once the valve 10M is in position, the instrument 70M is withdrawn from the chest (or another vascular access site) before the opening and incision are closed using conventional procedures. As will be appreciated by those skilled in the art, the valve 10M may be implanted using this procedure with minimal trauma to the heart H and without removing the damaged heart valve from the heart.

The instrument 70A shown in FIG. 5 is intended for use when implanting the valve 10A by a transluminal procedure through a vessel. It is envisioned this instrument 70A would be used when implanting an artificial valve in the aortic valve A. When used to implant an artificial valve 10A in an aortic valve A, the instrument 70A could be introduced through a femoral artery. The instrument 70A comprises a holder 90 having a hollow interior 92 sized for holding the artificial valve 10A when the frame 20 is in the collapsed configuration (e.g., less than about 6 mm) and an elongate flexible manipulator 94 attached to the holder for manipulating the holder through a vessel and into position adjacent the plurality of cusps C of the damaged heart valve A. Further, the instrument 70A has a flexible ejector, generally designated by 96, mounted in the hollow interior 92 of the holder 90 for ejecting the artificial heart valve 10A from the hollow interior of the holder into position between the cusps C of the damaged heart valve A. The manipulator 94 is used to manipulate the instrument 70A through the vessel. The ejector 96 includes a flat plunger tip 100 which engages the valve 10A, a push rod 102 attached to the tip for moving the tip forward in the holder 90 for ejecting the valve from the holder, and a handle 104 attached to the push rod opposite the plunger tip for gripping the ejector when ejecting the valve from the holder. Both manipulators 74,94 may be configured to be long and flexible enough to be pushed or pulled through a vessel and/or over a conventional guidewire as discussed in greater detail below.

To implant an artificial valve 10A using a transluminal procedure with instrument 70A, a small incision is made in a vessel (e.g., the femoral artery) leading to a heart H. An end 106 of the instrument 70A having the holder 90 is inserted through the incision made in the vessel and the end is pushed through the vessel and over a guidewire until the end is adjacent the cusps C of the damaged heart valve A. Once in position, the artificial valve 10A is ejected from the end 106 of the instrument 70A between the cusps C of the damaged heart valve A. As with the endothorascopic procedure described above, the transluminal procedure may be performed with minimal trauma to the heart H and without removing the damaged heart valve from the heart and without cardiopulmonary bypass or heart arrest.

Figure 6:
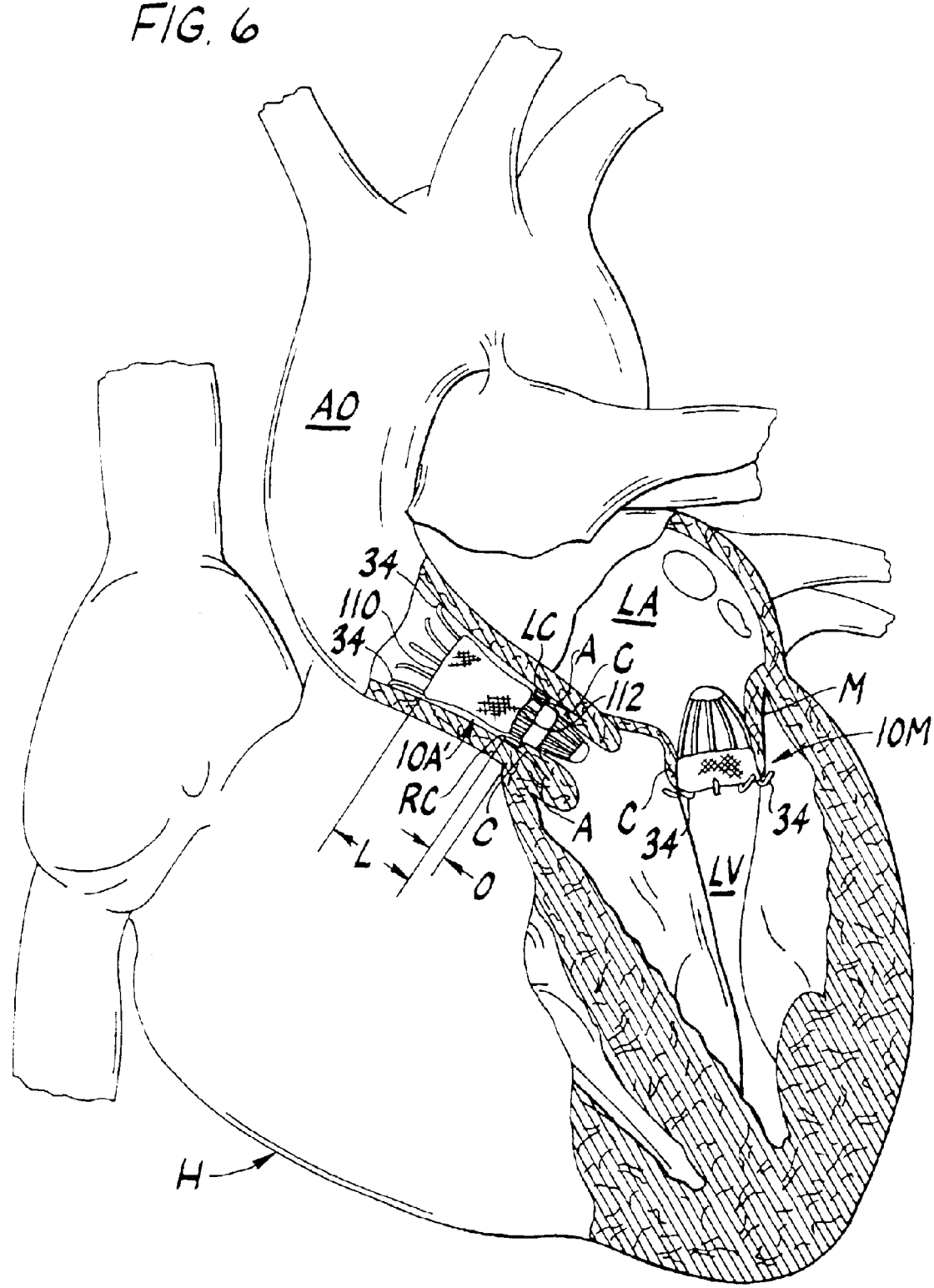
FIG. 6 is a front elevation of a heart in partial section showing artificial valves of the present invention.

A second embodiment of the aortic valve is generally designated by 10A' in FIG. 6. This second embodiment is identical to the aortic valve of the first embodiment except that it includes a second band 110 surrounding the frame 20 downstream from the first band 40. The second band 110 permits the frame elements 30 to be pushed together so the frame 20 can be collapsed to the collapsed configuration, but limits the maximum spacing between adjacent frame elements. It is envisioned that the second band 110 may be constructed similarly to the first band 40 and may be made from similar materials to the first band. As will be appreciated by those skilled in the art, the second band 100 of the aortic valve 10A' supports the tissue surrounding the downstream region (i.e., the ascending aorta) and prevents the tissue from distending. An opening 112 provided between the first and second bands 40, 110, respectively, corresponds to openings of the right and left coronary arteries (designated by RC, LC, respectively) which enter the aorta immediately above the cusps C of the native valve so the replacement valve does not obstruct blood flow through these openings. Although the opening 112 may have other widths O without departing from the scope of the present invention, in one embodiment the opening has a width of between about 5 mm and about 10 mm. Although the second band 110 may have other lengths L without departing from the scope of the present invention, in one embodiment the second band 110 has a length of between about 6 cm and about 12 cm. It is further envisioned that hooks (not shown) may be provided along the frame elements 30 adjacent the second band 110 to engage the tissue to further prevent distention of the tissue.

In yet another embodiment of the present invention illustrated in FIGS. 8 and 9, an artificial heart valve of another embodiment of the present invention, generally indicated by 210, includes a flexibly resilient frame, generally indicated by 220, having a plurality of peripheral anchors 234 for anchoring the frame in an expanded configuration, generally as set forth above. The flexibly resilient frame 220 includes frame elements 230 biased outward as set forth above. A central portion 236 of the frame 220 is centrally located between the plurality of peripheral anchors 234 of the frame. In addition, the artificial heart valve 210 includes a flexible valve element 222 attached to the central portion 236 of the frame having a convex upstream side 250 and a concave downstream side 252 opposite the upstream side. The valve element 222 moves in response to fluid pressure between an open position, with the valve element collapsed inward, and a closed position, with the element extended outward.

Figure 7:
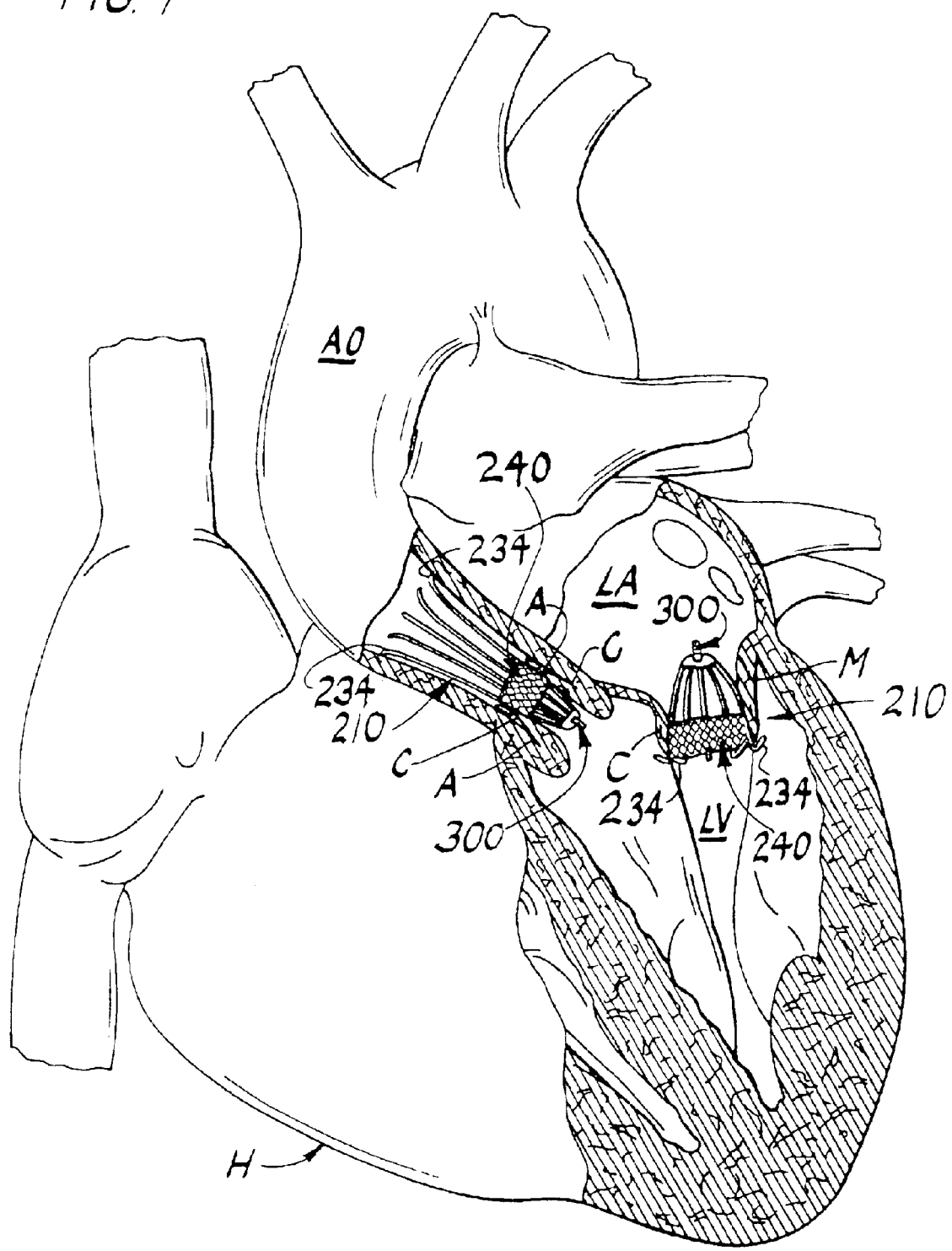
FIG. 7 is a front elevation of a heart in partial section showing two artificial valves of further embodiments of the present invention.

In addition, the artificial valve 210 may include a band, generally indicated by 240, extending around the frame elements 230 to limit outward movement of the frame elements to the expanded configuration and to sealingly engage adjacent heart H tissue (FIGS. 7 and 8). In one embodiment, the band 240 includes an inner portion 258 and an outer portion 260. The inner portion 258 is formed to limit outward movement of the frame elements 230 and to act as a sealing surface for the valve element 222 in its closed position, where the element extends outward to seal against the inner portion. The outer portion 260 at least partially surrounds the inner portion 258 and has a memory, such that when the frame elements 230 are forced inward to a collapsed configuration, the outer portion urges the inner portion inward to a position inside the frame elements. Preferably, the frame elements 230 are biased outward by a spring force sufficient to overcome the inward force of the outer portion 260, so that the frame elements maintain the frame 220 in the expanded configuration. The flexible valve element 222 is attached to the frame 220, and more particularly to the band 240, at several attachment points 256 around the frame. Thus, the valve element 222 forms flaps 257 extending between adjacent attachment points 256. The preferred embodiment of the valve, shown in FIG. 13, has three attachment points 256 and three flaps 257. It is contemplated that other numbers of attachment points 256 (e.g., 2, 4, 5, 6, etc.) may also be used without departing from the scope of the present invention. FIG. 13, however, shows a preferred embodiment having three equally spaced attachment points 256, forming three flaps 257. This configuration is thought to provide the maximum flow of blood through the valve 210 while maintaining flaps 257 that will close quickly when required. Flaps 257 of the three-flap preferred embodiment are also configured to be an optimal length circumferentially. The length of such flap 257 in the closed position, with the element extended outward, is approximately equal to 2.09r, where r is the radius of the valve. In the open position, with the valve element 222 collapsed inward, the ideal length for the valve flap 257 is 2r, which is approximately equal to 2.09r. The substantial congruence of these two lengths (2r and 2.09r) facilitates proper support of the valve element 222 without undue stress due to incongruence of optimal flap length between the open and closed positions.

In addition, it is envisioned the valve element 222 may be longitudinally pleated as depicted in FIGS. 11–13. Pleats 264 encourage proper folding of the valve element 222 when the valve 210 collapses (FIG. 10). The pleats 264 may be of a wide range of numbers and spacing. For example, the valve 210 of FIGS. 10 and 11 includes a valve element 222 having many pleats of uniform size and shape. The number of pleats 264 may be reduced or increased from what is shown in FIGS. 11 and 12, without departing from the scope of the present invention. Moreover, the spacing between the pleats 264 may be altered. For example, for an element 222 having pleats 264, half of the pleats may have wide spacing while the other half may have narrow spacing. These pleats may be alternated, for example, wide-narrow-wide-narrow etc. Other combinations of pleats 264 having relatively different spacing are also contemplated as within the scope of the present invention. Without wishing to be bound by any particular theory, it is envisioned that longitudinal pleats 264 may encourage laminar flow through the valve when in the open position, with the valve element 222 collapsed inward, as shown in FIG. 13.

The inner portion 258 preferably has a width B between about 4.0 mm and about 6.0 mm. The opposite sides of the band 240 are preferably spaced by a distance D of between about 21 mm and about 33 mm, depending upon the intended application of the artificial valve 210. This yields an artificial valve 210 with a perimeter in the expanded configuration of between about 60 mm and about 100 mm. In the collapsed configuration, the opposite sides of the band 240 are preferably spaced by a distance of no more than between about 6.0 mm and about 8.0 mm.

The inner portion 258 may comprise a material selected from the group consisting of PTFE, Dacron® velour material, Dacron® porous cloth, a synthetic polymer and biological source tissue. Alternately, non-synthetic materials may be used for the inner portion 258. Heterologous preserved tissues from bovine or porcine pericardium may be used as disclosed above. In addition, autologous tissues (i.e., those derived from a patient's own tissue) may be used as a substitute for synthetic or heterologous tissues. It is envisioned that the previously described band 240 and flexible valve element 222, described below, could be made from autologous tissues, thereby eliminating the possibility of immune system or foreign body rejection complications sometimes caused by synthetic material or heterologous tissue.

Figure 15:
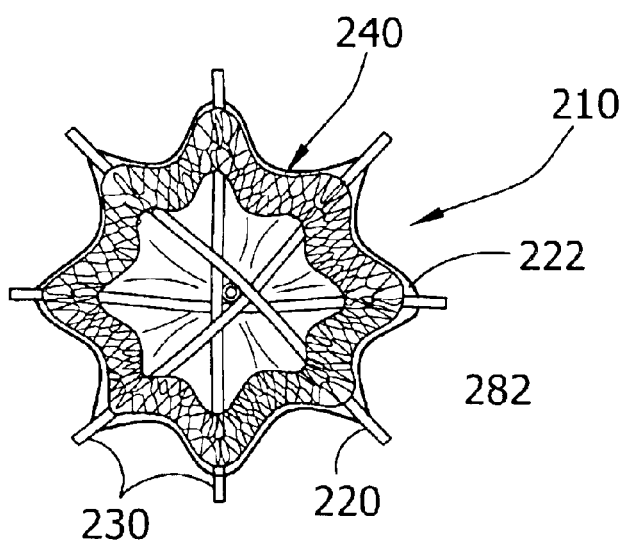
FIG. 15 is a top plan of the artificial valve of FIG. 8 partially collapsed.

The outer portion 260 has a width B' that is substantially similar, yet slightly wider than the inner portion. This larger width B' allows the outer portion 260 to attach to the frame elements 230 at several contact points 270 outside the opposite edges of the inner portion 258. The outer portion 260 preferably attaches to the frame elements 230 by laser welding, epoxy bonding or other means as would be readily understood by one skilled in the art, such that the outer portion 260 can move independent from the inner portion 258. Therefore, when the artificial valve 210 collapses or expands, the outer portion 260 and inner portion 258 are free to move independently, without binding upon one another. The outer portion 260 urges the inner portion 258 inward between the frame elements as shown in FIG. 15. This ensures that the inner portion 258 of the band 240 folds into the proper shape upon collapse of the artificial valve 210. The purpose of the outer portion 260 of the band 240 is to prevent the inner portion 258 from protruding outward beyond the frame elements 230 when the artificial valve 210 is collapsed. Without the outer portion 260, segments of the inner portion 258 located between the frame elements 230 would be free to flex either inward or outward as the frame elements 230 move inward. With the outer portion 260, the inner portion folds inward between the frame elements 230. The outer portion 260 essentially prevents the inner portion 258 from prolapsing outwardly as the valve collapses, which could impede loading of the artificial valve 210 into a holder 276, as will be described below. Folding the inner portion 258 inward also provides a smaller distance D between opposite sides of the band 240 when the artificial valve 210 is in the collapsed configuration. Moreover, the outer portion 260, due to its inherent material properties, provides a lower friction surface for the artificial valve 210 as it moves to and from the holder 276.

The outer portion 260 preferably comprises a braided mesh 282, in which thin filaments 284 are braided into a woven fabric (FIGS. 8 and 9). Such filaments 284 each preferably have a thickness of between about 0.05 mm and about 0.13 mm. The filaments 284 may comprise Nitinol superelastic alloy, stainless steel alloy, Elgiloy® alloy (available from Elgin National Watch Company of Elgin, Ill.), fiberglass, PTFE, polyester or Lycra® (available from E.I. duPont de Nemours and Company of Wilmington, Del.). The thin filaments 284 of the mesh 282 preferably move freely with respect to one another, such that the mesh may change its shape and size as the artificial valve 210 moves between its expanded and collapsed configurations. Where the material of the braided mesh 282 is a metal with shape memory, the outer portion 260 may be heat treated to set the unrestricted perimeter of the braided mesh to be smaller than the size of the desired collapsed configuration. Treating the braided mesh 282 to constrict to smaller than the collapsed configuration ensures that the braided mesh continues to exert a compressive force upon the artificial valve 210 irrespective of valve configuration. Therefore, for an artificial valve 210 having a collapsed dimension of between about 6.0 mm and about 8.0 mm, the braided mesh 282 preferably is heat treated to a dimension less than the collapsed valve dimension. Thus, by heat treating the braided mesh 282 of the outer portion 260 as described above, it biases the inner portion 258 and frame elements 230 inward in all configurations. Such inward forces caused by the outer portion 260 oppose the outward spring forces of the frame elements 230. As such, the outwardly directed force of the frame elements 230 are preferably greater than the inwardly directed force of the band 240 to ensure the artificial valve 210 will expand to its expanded configuration when released from its holder 276.

In an alternative embodiment depicted in FIG. 8A, the valve 210' comprises a thin strand 296, instead of a band 240, extending around the frame elements 230 to limit outward movement of the frame elements to their expanded configuration. The thin strand 296 functions in primarily the same way as the band 240. The strand 296 includes an inner portion 258' and an outer portion 260' substantially as disclosed above with respect to the band 240. The valve 210' of the alternative embodiment is identical to the valve 210 of the previously described embodiment in all other respects.

Figure 14:
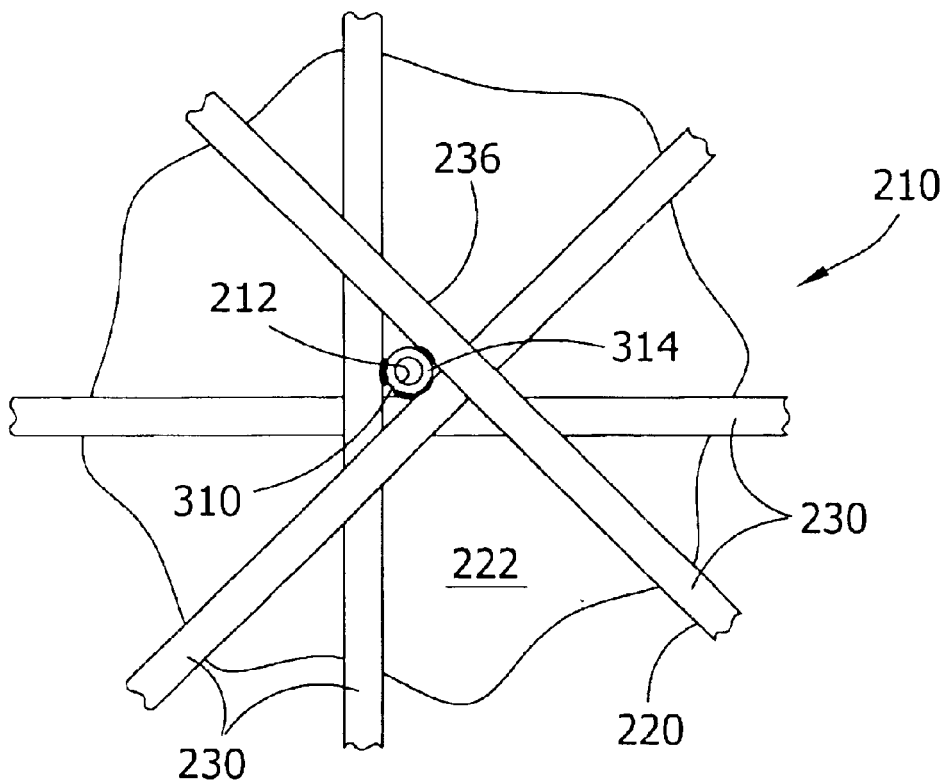
FIG. 14 is an enlarged partial top plan of the artificial valve of FIG. 8.
Figure 16:
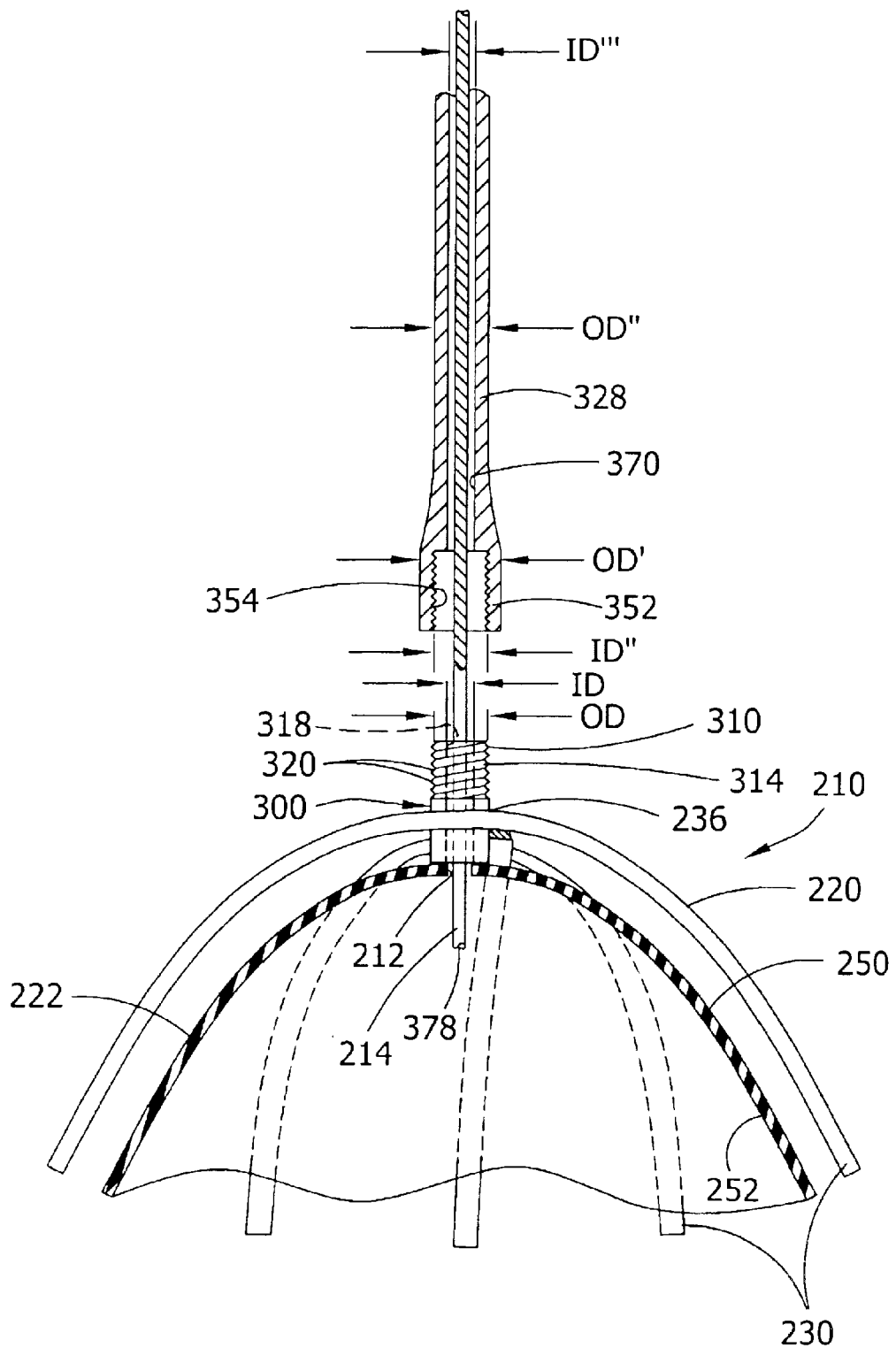
FIG. 16 is an enlarged partial section of an artificial valve and installer.

The frame 220 preferably includes a post 310, or more generally a mount, generally indicated by 300, for selectively connecting the artificial valve 210 to an instrument, generally indicated by 306 (FIG. 18). In one embodiment, the post 310 mounts on the frame 220 (FIGS. 8, 14, 16 and 17) and includes an opening 212 (FIG. 14) to allow an implement 214, such as a guide, or guidewire, as depicted in FIG. 16 and described in detail below, to pass through the valve 210. The opening 212 extends through at least one of the frame 220 and the valve element 222 for receiving the implement 214 (FIGS. 8 and 16). Although the opening 212 of the illustrated embodiment extends through the central portion 236 of the frame 220 and the valve element 222, it is envisioned that the opening 212 could extend through other portions of the artificial valve 210 without departing from the scope of the present invention. After removal of the implement 214, it is envisioned the opening 212 may provide surface washing to reduce a potential for blood to coagulate adjacent the downstream side (i.e., the concave side 252) of the valve element 222. It is further envisioned the opening 212 may be used even where an implement 214 is not needed to reduce potential for blood to coagulate adjacent the valve element 222. Although this opening 212 may have other dimensions without departing from the scope of the present invention, in one embodiment the opening has a width of between about 0.5 mm and about 1 mm, and more preferably a width of about 1 mm.

The post 318 may additionally include a releasable fastener 314. For example, the post 318 may include threads 320 (FIG. 16) for attaching the valve 210 to the instrument 306. Either the inside or outside of the post 318 may be threaded, but is preferably externally threaded, as shown in FIGS. 8 and 16. Preferably, the post 318 has an inner diameter ID of about 1.0 mm (FIG. 16) and an outer diameter OD of about 2.0 mm. The post 318 is also preferably right-hand threaded, although left-hand threads are contemplated as being within the scope of the present invention.

As illustrated in FIG. 18, the instrument 306 of the present invention further includes the holder 276, having a hollow interior 332 sized for holding the artificial valve 210 when the frame 220 of the valve is in the collapsed configuration. The holder 276 includes an outwardly flared end 336 for receiving the peripheral anchors 234 while the artificial valve 210 is within the holder. This shields the anchors 234 from engaging valvular or endocardial structures as the artificial valve 210 is retrieved into the holder 276 for repositioning, as will be discussed in greater detail below. In addition, the flared end 336 facilitates receiving the artificial valve 210 within the holder 276 by creating a smooth and gradual entry for the valve, such that the frame elements 230 may collapse more easily as the artificial valve is pulled into the holder by the instrument 306. The holder 276 additionally includes internal, longitudinal grooves 338 extending the length of the holder (FIGS. 10 and 19). This grooving 338 helps guide the frame elements 230 and anchors 234 into individual grooves as the valve 210 is ejected from or retrieved into the holder 276. By providing a groove 338 for each frame element 230, the valve 210 will collapse uniformly within the holder 276, thereby ensuring that the valve element 222 collapses properly, as shown in FIG. 10. The holder 276 is formed from a material sufficiently strong to limit outward movement of the frame elements 230 when the valve 210 is in the holder. An artificial valve 210 of the present invention is preferably collapsible to its collapsed configuration such that the dimension D' of the artificial valve is about 5 mm to about 8 mm. Thus, the holder 276 requires an inner dimension D' of at least about 5 mm to about 8 mm to receive the artificial valve 210 in its collapsed configuration. It is contemplated that the holder 276 will have an outer dimension OD''' of about 6 mm to about 9 mm along most of its length. The outwardly flared end 336 is formed to have a slightly larger dimension than the holder 276 (e.g., about 7 mm to about 10 mm) to accommodate the anchors 234. Although the holder 276 must be sufficiently strong to limit outward movement of the frame elements 230, once the valve 210 is removed, the holder may collapse slightly as it is removed from the body to ease its removal.

The instrument 306 further comprises an elongate manipulator 344 extending from the holder 276 for manipulating the holder into position between the upstream region and the downstream region. As shown in FIG. 18, the holder 276 and elongate manipulator 344 are of unitary construction, although it is contemplated that they may be formed separately and then joined. Depending upon the size of the patient and the entry point of the elongate manipulator 344 (e.g., femoral artery, femoral vein, jugular vein, endoscopic trans-thoracic), manipulators of different length are needed. The manipulator 344 must be long enough to allow the artificial valve 210 to reach the damaged heart valve, without having additional unnecessary length which may hinder remote movement of the manipulator. The elongate manipulator 344 preferably has a minimum inner dimension ID' of about 2.5 mm to about 3.0 mm to accommodate an installer 328, as described in detail below.

The elongate manipulator 344 is preferably formed of a material sufficiently flexible to allow bending as it passes through the body of the patient. In addition, the material is preferably sufficiently rigid such that the holder 276 at the end of the manipulator 344 moves in response to manual movements of the elongate manipulator. The elongate manipulator 344 is preferably both flexible for threading through the vessel of the patient, while still possessing the column strength required to push the elongate manipulator through the vessel. Materials capable of meeting such requirements include PTFE, polyurethane, polyvinyl or polyethylene combined with a radiopaque treatment. In addition, magnetically directed catheter guidance technology may also be applied to the elongate manipulator 344 to aid in guiding the manipulator through the vessel. One skilled in the art would readily understand how to apply such technology to the present invention. An example of magnetically directed catheter guidance technology is available from Stereotaxis, Inc. of St. Louis, Mo.

The elongate manipulator 344 further includes a hollow interior 348 shaped and sized to receive the installer 328. The installer is releasably attachable to the artificial heart valve 210 for maneuvering the artificial heart valve from the hollow interior 332 of the holder 276 into position between the upstream region and the downstream region of the damaged heart H. In one embodiment, an end 352 of the installer 328 includes an internally threaded portion 354 for threadably receiving the externally threaded post 310 of the valve 210. This allows the user to push the valve 210 from the holder 276 and selectively release the installer 328 from the post 310 of the valve by rotating the installer, thereby unscrewing the installer from the post. The installer 328 and elongate manipulator 344 may then be removed from the surgical field. Preferably, the internally threaded portion 354 would have an inner dimension ID'' of about 2.0 mm to match the outer dimension OD of the externally threaded post 310. In one embodiment, the end 352 of the installer 328 preferably has an outer dimension OD' of about 2.5 mm while the remaining portion of the installer has an outer dimension OD'' of about 2.0 mm.

Figure 17:
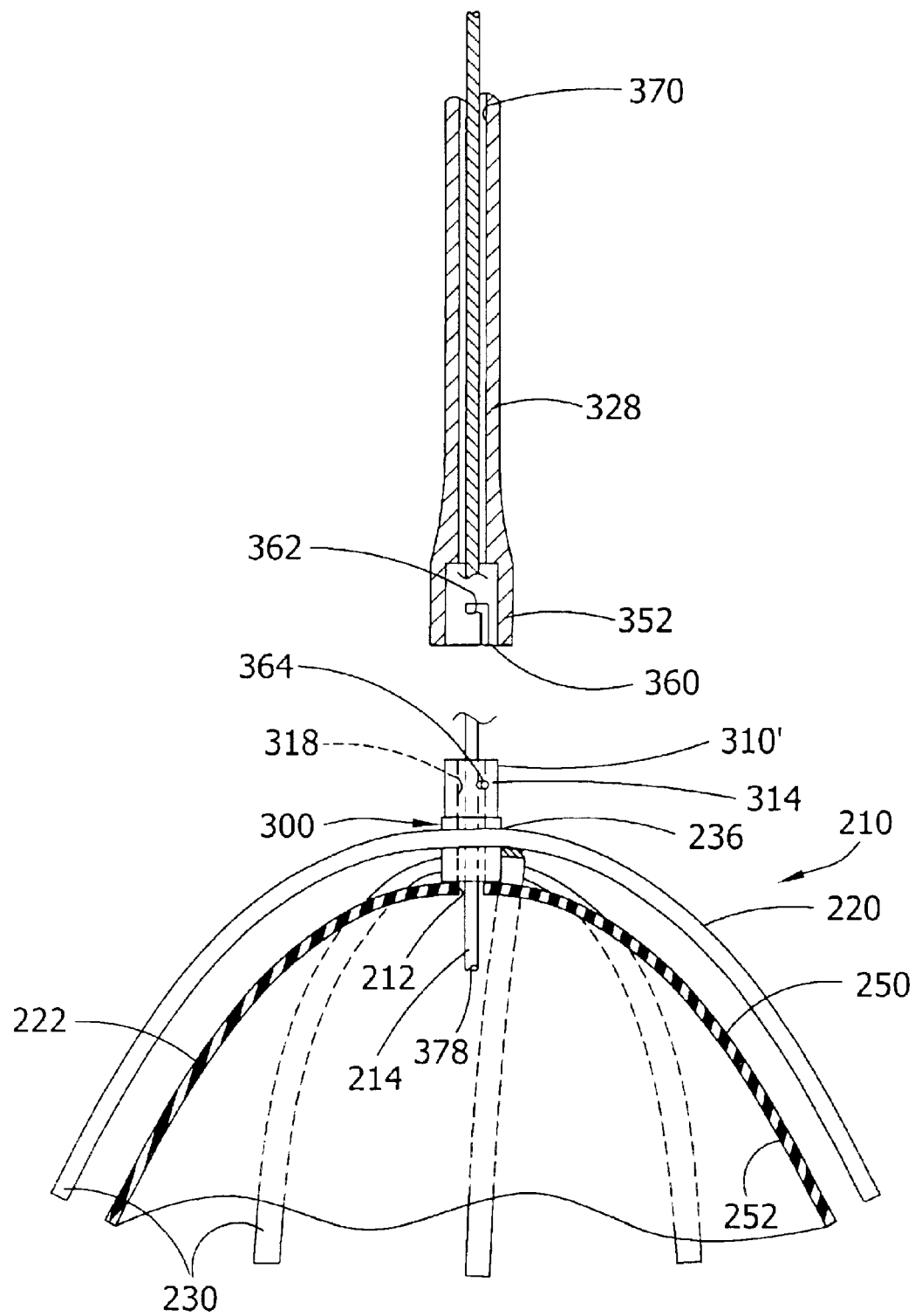
FIG. 17 is an enlarged partial section of an artificial valve and an installer of an alternative embodiment to that shown in FIG. 16.

In a different installer and post embodiment, the post 310' includes a bayonet fastener 360 as depicted in FIG. 17.

Rather than threading onto the installer 328, the bayonet fastener 360 includes a keyway 362 for receiving a key 364 extending from the post 310'. The key 364 and keyway 362 cooperate to maintain the installer 328 connected to the post 310'. To disengage the bayonet fastener 360, the user simply rotates the installer 328 and pulls, thereby allowing the key 364 to pass through and escape from the keyway 362. The positions of the keyway 362 and key 364 may switch, such that the post 310' includes the keyway and the installer includes the key, without departing from the scope of the present invention.

Returning to the previous embodiment, illustrated in FIG. 16, the installer 328 further includes an open central channel 370 passing through the length of the installer. This channel 370 permits passage of implements 214 (e.g., guides, catheters, etc.) to aid in installing the artificial valve 210. Preferably, the channel 370 has an inner dimension ID'" of about 1.0 mm for accommodating implements 214 of up to that dimension. The ID'" and OD" may vary somewhat, however, depending upon the particular valvular implant procedure. The sizes indicated here are for illustrative purposes only, and one skilled in the art would readily understand that such dimensions may vary without departing from the scope of the present invention. The installer 328 is preferably fabricated from any type of biocompatible metallic or elastomeric material. Preferably, the installer 328 is also of a flexible construction and is radiopaque.

The guide 214 of the present invention aids in guiding the artificial valve 210 through a body of a patient and into position between the upstream region and the downstream region of the damaged heart H. The guide 214 is elongate, flexible and sized for receipt within the opening 212 to guide the valve 210 into position. As discussed above, the guide 214 is much smaller than the elongate manipulator 344, preferably formed with a dimension no greater than about 1.0 mm. Because the guide 214 is much smaller than the manipulator 344, it can be more easily maneuvered through the vessels of the patient to the heart H. Once the guide 214 is placed within the patient and guided to the area of interest, the manipulator 344 and installer 328 may be threaded onto the guide for passage to the area of surgical interest as explained below.

The present invention may further comprise an implement 214 functioning as a vascular catheter 214. The vascular catheter 214 may include a sensor for registering and sending a signal through the vascular catheter for vascular monitoring. Such a sensor may preferably comprise a pressure sensor or an oximetry sensor. In addition, the vascular catheter 214 may comprise a dye injector for injecting dye into the heart H. Each of these vascular catheters 214 performs a specific function, readily understood by one skilled in the art.

The artificial valve 210 of the present invention is preferably installed in an antegrade orientation, meaning that the valve is ejected from the holder 276 in the direction of blood flow. Such antegrade applications include implantation to the mitral M, pulmonary or tricuspid valves via transvenous routes, typically via the femoral vein. For the mitral valve M implantation, the artificial valve 210 typically passes through the femoral vein and into the right atrium. From there, the surgeon performs a septostomy to create a small atrial septal perforation (i.e., atrial septal defect (ASD)) between the right atrium and left atrium LA to gain access to the left atrium. Such an ASD may require closure if unacceptable levels of shunting across the ASD are shown by testing (e.g., Doppler color flow imaging, blood oximetry, excessive pressure gradients). Such an antegrade orientation will apply to both endoscopic and open thoracotomy implants into the mitral valve M through a left closed atriotomy beating heart procedure without cardio pulmonary bypass and cardioplegia or a left open atriotomy with cardio pulmonary bypass and cardioplegia.

It is envisioned that the previously described instrument 306 would permit implantation of an artificial valve 210 by a transseptal procedure or a retrograde non-transseptal procedure. Transseptal access is conventionally used for balloon valvuloplasty of the mitral valve M with an Inoue single balloon catheter or another type of balloon catheter (e.g., Mansfield balloon catheter, available from Mansfield Scientific, Inc., of Mansfield, Mass.). Each of these procedures requires the intentional, controlled creation of an ASD between the right and left atria. Such a septostomy is required for the transseptal procedures noted above. The initial penetration of the atrial septum is typically performed using a Brockenbrough® catheter/needle (available from C.R. Bard, Inc. of Murray Hill, N.J.), which provides an atrial septal penetration of about 8.5 French (Fr.) (2.8 mm). Further dilation may then be provided using a 24 Fr. (8.0 mm) dilation catheter balloon about 30 mm in length. For the Inoue balloon, a 14 Fr. (4.7 mm) or 16 Fr. (5.3 mm) dialator sheath may be advanced through the septum after the initial penetration. Such procedures provide a relatively low incidence rate of a significant residual ASD. Such rates tend to fall in a range of about ten to about fifteen percent. Identifying such residual ASDs is readily accomplished by measuring transluminal pressure gradients or blood oximetry within the heart H. For example, an excessive left atrium to right atrium transmural pressure gradient may indicate a shunt between atria. Similarly, blood oximetry indicators, such as an oxygen saturation in the right atrium more than about seven percent by volume greater than blood in the superior vena cava, may also indicate a shunt. However, what may in fact be an insignificant residual ASD can present as a false positive on a color-flow Doppler study, but this can be further analyzed by a Valsalva maneuver bubble test, as one skilled in the art would appreciate. Finally, although the projected size of ASDs are quite large when considering the balloon dimensions noted above, the atrial septum in the area of penetration (i.e., fossa ovalis) is elastic, thereby contracting and closing the septostomy after removal of a balloon or other surgical tool. These surgically created defects typically close and heal spontaneously, but may also be closed with some type of closure device if required. One skilled in the art would readily understand how to make such determinations concerning possible shunts.

Aortic valve A access with an antegrade valve implant procedure is also possible by the method disclosed above (i.e., femoral vein to right atrium to left atrium LA) with the additional passage of the artificial valve through the mitral valve M and into the left ventricle LV. Alternately, access to the aortic valve A is possible in a retrograde configuration (e.g., from the femoral artery), as described above with respect to FIG. 5. Such an installation would not include the use of a releasable fastener, but would incorporate a plunger tip 80 and push rod 82 as set forth above. The push rod 82 could be configured with a central channel, however, such that the advantages of the presently disclosed guide 214 may be adapted to retrograde applications. The artificial valve 210, push rod 82 and manipulator 74 may be threaded onto the guide 214 to facilitate positioning the artificial valve adjacent the damaged aortic valve A. Such an arrangement also provides access for a vascular catheter 214 as described herein, such that pressure readings and dye injections may be made near the aortic valve A implant site.

In addition, the present invention is directed to an endothoracoscopic method of inserting the artificial valve 210 described above between a plurality of cusps C of a damaged heart valve. The method comprises multiple steps, some of which are not depicted in the figures because one skilled in the art would readily understand how to perform such steps by referencing the claims and specification only. First, an opening is made in a chest wall of a patient. Then, an incision is made in the heart H of the patient. Determining the location, orientation and size of such an opening and incision are well within the skill and understanding of one skilled in the art. The end 336 of the elongate instrument 306 is then inserted through the opening made in the chest wall and the incision made in the heart H. The surgeon may then position the inserted end 336 of the instrument adjacent the plurality of cusps C of the damaged heart valve. This procedure is particularly applicable to the mitral valve or the tricuspid valve. The artificial valve 210 within the instrument 306 may then be ejected from the end 336 of the instrument and positioned adjacent the plurality of cusps C of the damaged heart valve. If placed properly, this ejection will place the artificial valve 210 into a position between the plurality of cusps C of the damaged heart valve without removing the damaged heart valve from the heart H and without cardiopulmonary bypass or cardioplegia. With the artificial valve 210 properly placed within the heart H, the surgeon may then remove the instrument 306 from the patient and complete the surgery.

In some instances, however, the position of the artificial valve 210 in the heart H may not be optimal after the first ejection from the instrument 306. In those cases, the surgeon may then retrieve the artificial valve 210 into the end 336 of the instrument 306. Retrieving the artificial valve 210 into the instrument 306 is accomplished by advancing the elongate manipulator 344 over the installer 328. Such relative movement between the installer 328 and the elongate manipulator 344 retrieves the artificial valve 210 to within the holder 276, thereby forcing the valve from its expanded configuration to its collapsed configuration. The surgeon may then reposition the inserted end 336 of the instrument 306 adjacent the plurality of cusps C of the damaged heart valve and eject the repositioned artificial valve 210 from the end of the instrument again. This provides the surgeon with the flexibility to reposition the artificial valve 210 between the plurality of cusps C of the damaged heart valve multiple times until the positioning is optimal.

In yet another method of the present invention, an artificial valve 210 as described above may be inserted transluminally and placed between a plurality of cusps C of a damaged heart valve. Such a method is similar to the method disclosed immediately above, except that an incision is made in a vessel leading to the heart H, an end 336 of an elongate flexible instrument 306 is inserted through the incision made in the vessel and the end of the instrument is pushed through the vessel to be positioned adjacent the plurality of cusps C of the damaged heart valve. Once in position, the method is essentially the same. The method provides a surgeon with the flexibility to position and reposition the artificial valve 210 within the heart H.

In another method of the present invention, the artificial valve 210 is again inserted transluminally after making an incision in a vessel leading to the heart H. Here, however, an end 378 of the guide 214 is first inserted through the incision made in the vessel. The guide 214 is preferably smaller in its width dimension than the instrument 306 that will be inserted later. The smaller dimension of the guide 214 simplifies the task of pushing the guide through the vessel to the heart H of the patient, especially where the vein is of a smaller inner dimension. Once the guide 214 is in the proper position near the heart valve of the patient, the elongate flexible instrument 306 with hollow interior 348 is threaded onto the guide. The end 336 of the elongate flexible instrument 306 may then be threaded through the incision made in the vessel and pushed through the vessel along the guide 214 until the end is adjacent the plurality of cusps C of the damaged heart valve. Because the guide 214 has delineated a path for the instrument 306 to the heart H, the instrument may more easily pass through the vessel. Once in position, the artificial valve 210 may be ejected from the end 336 of the instrument 306 positioned adjacent the plurality of cusps C of the damaged heart valve into a position between the plurality of cusps of the damaged heart valve without removing the damaged heart valve from the heart H.

As will be appreciated by those skilled in the art, the valves and instruments described above permit "beating heart" procedures (i.e., without cardiopulmonary bypass or cardioplegic arrest) in part due to the relatively small size of the valves and instruments. Further, the valves described above permit implantation without removal of the native valves. The valves also permit some correction of valvular stenosis along with correction of regurgitant valvular disease. It is further envisioned that the valves described above may be coated with heparin or other protective coatings and immune suppressant coatings (e.g., rapamycin coating) to reduce coagulation or immune inflammatory response initiation.

It is envisioned that the valves of the present invention may be suitable for implant in pediatric patients due to their small size and substantially unrestricted flow characteristics. Further, because the valves adaptively expand, they are capable of expanding to fit a growing child.

It is further envisioned that rapidly implanting the valves of the present invention using an endothoracoscopic technique may provide a suitable remedy of acute papillary muscle dysfunction due to major chordal rupture or frank papillary muscle infarction.

In heavily calcified native valves, implantation of the valve described above could remedy regurgitant disease without disturbing the calcific deposits.

When used in the mitral M site, the valve described above avoids problems associated with valve cusp stents and fabric arms present in prior art bioprosthetic valves. Also use of the valve described above at the mitral M site eliminates removal of or damage to papillary muscles and all of the chordae tendinae thereby preserving systolic apical movement. Still further, the valve described above is compliant and capable of regurgitant control in cases of ischemic mitral regurgitation.

When used in the aortic valve A site, placement of the valve may be controlled using fluoroscopic guidance or echocardiographic guidance to ensure the native cusps C are positioned in the valve sinuses and the coronary openings above the valve site are not obstructed. It is envisioned that a conventional dye injection technique may be used to identify the coronary openings.

When used to implant the valve in either the Mitral or Atrial site, fluoroscopy and/or echocardiographic studies may be used to verify proper device positioning prior to release of the artificial valve.

In view of the above, it will be seen that the several objects of the invention are achieved and other advantageous results attained.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An artificial valve for repairing a damaged heart valve having a plurality of cusps separating an upstream region from a downstream region, said artificial valve comprising:
   a flexibly resilient frame sized and shaped for insertion in a position between the upstream region and the downstream region, the frame having a plurality of peripheral anchors for anchoring the frame in the position between the upstream region and the downstream region and a central portion located along a centerline extending between the plurality of peripheral anchors and between the upstream region and the downstream region when said frame is inserted in the position between the upstream region and the downstream region;
   a flexible valve element attached to the central portion of the frame having an upstream side facing said upstream region when the frame is anchored in the position between the upstream region and the downstream region and a downstream side opposite the upstream side facing said downstream region when the frame is anchored in the position between the upstream region and the downstream region, said flexible valve element moving in response to a difference between fluid pressure in said upstream region and fluid pressure in said downstream region between an open position in which the flexible valve element permits downstream flow between said upstream region and said downstream region and a closed position in which the flexible valve element blocks flow reversal from said downstream region to said upstream region, wherein the flexible valve element moves to the open position when fluid pressure in said upstream region is greater than fluid pressure in said downstream region to permit downstream flow from said upstream region to said downstream region and the flexible valve element moves to the closed position when fluid pressure in said downstream region is greater than fluid pressure in said upstream region to prevent flow reversal from said downstream region to said upstream region; and
   an opening extending through at least one of said frame and said flexible valve element for receiving an implement.

2. An artificial valve as set forth in claim 1 wherein said opening extends through the central portion of the frame and the flexible valve element.

3. An artificial valve as set forth in claim 2 further comprising a releasable fastener mounted on the frame for selectively connecting the valve to an instrument.

4. An artificial valve as set forth in claim 3 wherein the fastener comprises a hollow post mounted on the central portion of the frame coaxial with the opening.

5. An artificial valve as set forth in claim 4 wherein said fastener comprises a threaded fastener.

6. An artificial valve as set forth in claim 5 wherein said post is externally threaded.

7. An artificial valve as set forth in claim 4 wherein said fastener comprises a bayonet fastener.

8. An artificial valve as set forth in claim 1 wherein said flexibly resilient frame includes frame elements extending outward from the central portion, said frame elements being biased outward to engage the heart tissue and hold the frame in an expanded configuration in the position between the upstream region and the downstream region.

9. An artificial valve as set forth in claim 8 further comprising a band extending around the frame elements to limit outward movement of the frame elements to the expanded configuration and to sealingly engage adjacent heart tissue.

10. An artificial valve as set forth in claim 9 wherein said band includes an inner portion formed to limit outward movement of the frame elements, and an outer portion at least partially surrounding said inner portion and being biased inward, such that when the frame elements are forced inward to a collapsed configuration, the outer portion urges the inner portion inward to a position inside the frame elements.

11. An artificial valve as set forth in claim 10 wherein the frame elements are biased outward by a spring force sufficient to overcome the inward bias of the outer portion, so that the outward spring force maintains the frame in the expanded configuration.

12. An artificial valve as set forth in claim 11 wherein said outer portion comprises a braided mesh.

13. An artificial valve as set forth in claim 12 wherein said braided mesh comprises a woven fabric of filaments, each having a width of between about 0.05 mm and about 0.13 mm.

14. An artificial valve as set forth in claim 12 wherein said braided mesh comprises a material selected from the group consisting of Nitinol superelastic alloy, stainless steel alloy, Elgiloy® alloy, fiberglass, PTFE, polyester and Lycra®.

15. An artificial valve as set forth in claim 10 wherein said inner portion comprises a material selected from the group consisting of PTFE, Dacron® velour, Dacron® porous cloth, a synthetic polymer and biological source tissue.

16. A artificial valve as set forth in claim 8 further comprising a thin strand extending around the frame elements to limit outward movement of the frame elements to the expanded configuration.

17. An endothoracoscopic method of inserting an artificial valve as set forth in claim 1 between a plurality of cusps of a damaged heart valve, said method comprising the steps of:
   making an opening in a chest wall of a patient;
   making an incision in a heart of the patient;
   inserting an end of an elongate instrument through the opening made in the chest wall and the incision made in the heart;
   positioning the inserted end of the instrument adjacent the plurality of cusps of the damaged heart valve;
   ejecting an artificial valve from the end of the instrument positioned adjacent the plurality of cusps of the damaged heart valve into a position between said plurality of cusps of the damaged heart valve without removing the damaged heart valve from the heart;
   retrieving the artificial valve into the end of the instrument;
   repositioning the inserted end of the instrument adjacent the plurality of cusps of the damaged heart valve; and
   ejecting the repositioned artificial valve from the end of the instrument positioned adjacent the plurality of cusps of the damaged heart valve into position between said plurality of cusps of the damaged heart valve without removing the damaged heart valve from the heart.

18. A transluminal method of inserting an artificial valve as set forth in claim 1 between a plurality of cusps of a damaged heart valve, said method comprising the steps of:

making an incision in a vessel leading to the heart;

inserting an end of an elongate flexible instrument through the incision made in the vessel;

pushing the end of the instrument through the vessel;

positioning the end adjacent the plurality of cusps of the damaged heart valve;

ejecting an artificial valve from the end of the instrument positioned adjacent the plurality of cusps of the damaged heart valve into a position between said plurality of cusps of the damaged heart valve without removing the damaged heart valve from the heart;

retrieving the artificial valve into the end of the instrument;

repositioning the inserted end of the instrument adjacent the plurality of cusps of the damaged heart valve; and ejecting the repositioned artificial valve from the end of the instrument positioned adjacent the plurality of cusps of the damaged heart valve into position between said plurality of cusps of the damaged heart valve without removing the damaged heart valve from the heart.

19. A transluminal method as set forth in claim 18 further comprising performing a septostomy between the atria of the heart and pushing the instrument through an atrial septal perforation created by the septostomy.

20. A transluminal method of inserting an artificial valve as set forth in claim 1 between a plurality of cusps of a damaged heart valve, said method comprising the steps of:

making an incision in a vessel leading to the heart;

inserting an end of a guide through the incision made in the vessel;

pushing the guide through the vessel;

threading an elongate flexible instrument having a hollow interior onto the guide;

inserting an end of the elongate flexible instrument through the incision made in the vessel;

pushing the end of the instrument through the vessel along the guide until the end is adjacent the plurality of cusps of the damaged heart valve; and ejecting an artificial valve from the end of the instrument positioned adjacent the plurality of cusps of the damaged heart valve into a position between said plurality of cusps of the damaged heart valve without removing the damaged heart valve from the heart.

21. A transluminal method as set forth in claim 20 further comprising performing a septostomy between the atria of the heart and pushing the instrument through an atrial septal perforation created by the septostomy.

22. An artificial valve for repairing a damaged heart valve having a plurality of cusps separating an upstream region from a downstream region, said artificial valve comprising:

a flexibly resilient frame sized and shaped for insertion in a position between the upstream region and the downstream region, the frame having a plurality of peripheral anchors for anchoring the frame in the position between the upstream region and the downstream region;

a flexible valve element fixedly attached to the frame so that at least a portion of the element is substantially immobile with respect to at least a portion of the frame, said element having a convex upstream side facing said upstream region when the frame is anchored in the position between the upstream region and the downstream region and a concave downstream side opposite the upstream side facing said downstream region when the frame is anchored in the position between the upstream region and the downstream region, said flexible valve element moving in response to a difference between fluid pressure in said upstream region and fluid pressure in said downstream region between an open position in which the flexible valve element permits downstream flow between said upstream region and said downstream region and a closed position in which the flexible valve element blocks flow reversal from said downstream region to said upstream region, wherein the flexible valve element moves to the open position when fluid pressure in said upstream region is greater than fluid pressure in said downstream region to permit downstream flow from said upstream region to said downstream region and the flexible valve element moves to the closed position when fluid pressure in said downstream region is greater than fluid pressure in said upstream region to prevent flow reversal from said downstream region to said upstream region; and an opening extending through at least one of said frame and the flexible valve element.

23. An artificial valve as set forth in claim 22 further comprising a releasable fastener mounted on the frame for selectively connecting the valve to an instrument.

24. An artificial valve as set forth in claim 23 wherein the fastener comprises a hollow post mounted on the frame coaxial with the opening.

25. An artificial valve as set forth in claim 24 wherein said fastener comprises a threaded fastener.

26. An artificial valve as set forth in claim 25 wherein said post is externally threaded.

27. An artificial valve as set forth in claim 24 wherein said fastener comprises a bayonet fastener.

28. An artificial valve as set forth in claim 27 wherein said flexibly resilient frame includes frame elements extending outward from the central portion, said frame elements being biased outward to engage the heart tissue and hold the frame in an expanded configuration in the position between the upstream region and the downstream region.

29. An artificial valve as set forth in claim 28 further comprising a band extending around the frame elements to limit outward movement of the frame elements to the expanded configuration and to sealingly engage adjacent heart tissue and form a seal with the heart.

30. An artificial valve as set forth in claim 29 wherein said band includes a inner portion formed to limit outward movement of the frame elements, and an outer portion at least partially surrounding said inner portion and being biased inward, such that when the frame elements are forced inward to a collapsed configuration, the outer portion urges the inner portion inward to a position inside the frame elements.

31. In combination, an artificial valve for repairing a damaged heart valve having a plurality of cusps separating an upstream region from a downstream region, and a guide for guiding the artificial valve between the upstream region and the downstream region, said combination comprising:

said artificial valve including a flexibly resilient frame sized and shaped for insertion between the upstream region and the downstream region, the frame having a plurality of peripheral anchors for anchoring the frame between the upstream region and the downstream region and a central portion located along a centerline extending between the plurality of peripheral anchors, a flexible valve element fixedly attached to the central portion of the frame so that at least a portion of the element is substantially immobile with respect to the central portion of the frame, said element having an upstream side fading said upstream region when the frame is anchored between the upstream region and the downstream region and a downstream side opposite the upstream side facing said downstream region when the frame is anchored between the upstream region and the downstream region, said flexible valve element moving in response to a difference between fluid pressure in said upstream region and fluid pressure in said downstream region between an open position in which the flexible valve element permits downstream flow between said upstream region and said downstream region and a closed position in which the flexible valve element blocks flow reversal from said downstream region to said upstream region, wherein the flexible valve element moves to the open position when fluid pressure in said upstream region is greater than fluid pressure in said downstream region to permit downstream flow from said upstream region to said downstream region and the flexible valve element moves to the closed position when fluid pressure in said downstream region is greater than fluid pressure in said upstream region to prevent flow reversal from said downstream region to said upstream region, and an opening extending through at least one of said frame and the flexible valve element; and said flexible, elongate guide sized for receipt within the opening to guide the valve into position.

32. A combination as set forth in claim 31 further comprising a holder having a hollow interior sized for holding the artificial valve when the frame is in the collapsed configuration.

33. A combination as set forth in claim 32 further comprising an elongate manipulator attached to the holder for manipulating the holder into position between the upstream region and the downstream region.

34. A combination as set forth in claim 33 further comprising an installer received within the hollow interior of the holder and releasably attachable to the artificial heart valve for maneuvering the artificial heart valve from the hollow interior of the holder into position between the upstream region and the downstream region.

35. A combination as set forth in claim 32 wherein the holder comprises an outwardly flared end for receiving the artificial valve within the holder.

36. A combination as set forth in claim 32 wherein the holder comprises internal, longitudinal grooving for guiding the flexibly resilient frame.

37. A combination as set forth in claim 31 further comprising a vascular catheter.

38. In combination, an artificial valve for repairing a damaged heart valve having a plurality of cusps separating an upstream region from a downstream region, and an instrument for inserting the artificial valve between the upstream region and the downstream region, said combination comprising:

said artificial valve including a flexibly resilient frame sized and shaped for insertion between the upstream region and the downstream region, the frame having a plurality of peripheral anchors for anchoring the frame between the upstream region and the downstream region and a central portion located between the plurality of peripheral anchors, and a flexible valve element fixedly attached to the frame so that at least a portion of the element is substantially immobile with respect to the central portion of the frame, said element having an upstream side facing said upstream region when the frame is anchored between the upstream region and the downstream region and a downstream side opposite the upstream side facing said downstream region when the frame is anchored between the upstream region and the downstream region, said flexible valve element moving in response to a difference between fluid pressure in said upstream region and fluid pressure in said downstream region between an open position in which the flexible valve element permits downstream flow between said upstream region and said downstream region and a closed position in which the flexible valve element blocks flow reversal from said downstream region to said upstream region, wherein the flexible valve element moves to the open position when fluid pressure in said upstream region is greater than fluid pressure in said downstream region to permit downstream flow from said upstream region to said downstream region and the flexible valve element moves to the closed position when fluid pressure in said downstream region is greater than fluid pressure in said upstream region to prevent flow reversal from said downstream region to said upstream region, and an opening extending through at least one of said frame and the flexible valve element; and an instrument including a holder having a hollow interior sized for holding the artificial valve when the frame is in a collapsed configuration, an elongate manipulator attached to the holder for manipulating the holder into position between the upstream region and the downstream region, and an installer received within the hollow interior of the holder and releasably attachable to the frame of the artificial heart valve for maneuvering the artificial heart valve from the hollow interior of the holder into position between the upstream region and the downstream region.

39. A combination as set forth in claim 38 wherein the frame includes a mount for selectively connecting the valve to the instrument.

40. A combination as set forth in claim 39 wherein the mount comprises a post mounted on the frame.

41. A combination as set forth in claim 40 wherein said post comprises a threaded fastener.

42. A combination as set forth in claim 41 wherein said post is externally threaded.

43. A combination as set forth in claim 42 wherein said installer includes an internally threaded portion for threadably receiving said externally threaded post.

44. A combination as set forth in claim 40 wherein said post comprises a bayonet fastener.

45. A combination as set forth in claim 38 wherein said holder has an outwardly flared end for receiving the peripheral anchors when the artificial valve is within the holder.

46. A combination as set forth in claim 38 wherein the holder comprises internal, longitudinal grooving for guiding the flexibly resilient frame.

* * * * *